(12) United States Patent
Karasawa et al.

(10) Patent No.: US 12,059,303 B2
(45) Date of Patent: Aug. 13, 2024

(54) ULTRASOUND SYSTEM AND METHOD OF CONTROLLING ULTRASOUND SYSTEM

(71) Applicant: FUJIFILM Corporation, Tokyo (JP)

(72) Inventors: Hiroyuki Karasawa, Kanagawa (JP); Keiji Tsubota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 285 days.

(21) Appl. No.: 17/347,246

(22) Filed: Jun. 14, 2021

(65) Prior Publication Data

US 2021/0298720 A1 Sep. 30, 2021

Related U.S. Application Data

(63) Continuation of application No. PCT/JP2019/049778, filed on Dec. 19, 2019.

(30) Foreign Application Priority Data

Jan. 15, 2019 (JP) .................................. 2019-004702

(51) Int. Cl.
*A61B 8/08* (2006.01)
*A61B 8/00* (2006.01)
*H04N 13/344* (2018.01)

(52) U.S. Cl.
CPC .......... *A61B 8/5207* (2013.01); *A61B 8/4472* (2013.01); *A61B 8/4494* (2013.01);
(Continued)

(58) Field of Classification Search
CPC ... A61B 8/5207; A61B 8/4472; A61B 8/4494; A61B 8/462; A61B 8/565; A61B 8/4245;
(Continued)

(56) References Cited

U.S. PATENT DOCUMENTS

2002/0120193 A1   8/2002  Chiang et al.
2005/0228281 A1* 10/2005  Nefos ...................... A61B 8/08
                                                        600/446
(Continued)

FOREIGN PATENT DOCUMENTS

JP    2010-057562 A    3/2010
JP    2011-183056 A    9/2011
(Continued)

OTHER PUBLICATIONS

An Office Action; "Notice of Reasons for Refusal," mailed by the Japanese Patent Office dated Mar. 8, 2022, which corresponds to Japanese Patent Application No. 2020-566165 and is related to U.S. Appl. No. 17/347,246 with English language translation.
(Continued)

*Primary Examiner* — Alexei Bykhovski
(74) *Attorney, Agent, or Firm* — Studebaker & Brackett PC

(57) ABSTRACT

An ultrasound system (1) has a configuration in which a mobile information terminal (3) is connected to an ultrasound probe (2) and a head-mounted display (4) in a wireless manner. The ultrasound probe (2) includes an image information data generation unit (19) that generates image information data. The mobile information terminal (3) includes a mobile information terminal-side display unit (34), an operation image generation unit (37) that generates an operation image for an input operation, and a head-mounted display data generation unit (36) that generates head-mounted display data from the image information data. The head-mounted display (4) displays a head-mounted display ultrasound image based on the head-mounted display data.

20 Claims, 15 Drawing Sheets

(52) U.S. Cl.
CPC .............. *A61B 8/462* (2013.01); *A61B 8/565* (2013.01); *H04N 13/344* (2018.05)

(58) Field of Classification Search
CPC ......... A61B 8/463; A61B 8/464; A61B 8/467; A61B 8/4411; A61B 8/4427; A61B 8/485; A61B 8/486; A61B 8/488; A61B 8/5269; A61B 8/56; A61B 8/54; A61B 8/461; H04N 13/344; G06F 3/14
See application file for complete search history.

(56) References Cited

U.S. PATENT DOCUMENTS

| | | | | |
|---|---|---|---|---|
| 2010/0079356 | A1* | 4/2010 | Hoellwarth | H04B 1/385 |
| | | | | 345/8 |
| 2010/0168576 | A1* | 7/2010 | Poland | G01S 7/5208 |
| | | | | 600/443 |
| 2011/0245670 | A1 | 10/2011 | Tashiro et al. | |
| 2012/0050275 | A1* | 3/2012 | Matsui | H04N 21/472 |
| | | | | 345/419 |
| 2015/0049907 | A1* | 2/2015 | Hong | A61B 90/36 |
| | | | | 382/103 |
| 2015/0080729 | A1* | 3/2015 | Miyachi | A61B 8/0891 |
| | | | | 600/443 |
| 2016/0081667 | A1* | 3/2016 | Azegami | G01S 7/52098 |
| | | | | 600/443 |
| 2016/0100824 | A1* | 4/2016 | Kim | A61B 8/461 |
| | | | | 600/437 |
| 2017/0295361 | A1* | 10/2017 | Dashwood | H04N 13/344 |
| 2018/0078239 | A1 | 3/2018 | Ball et al. | |
| 2018/0125458 | A1 | 5/2018 | Takagi et al. | |
| 2018/0293041 | A1* | 10/2018 | Harviainen | G06F 3/147 |
| 2019/0068944 | A1* | 2/2019 | Zhang | G02B 27/0176 |

FOREIGN PATENT DOCUMENTS

| | | | |
|---|---|---|---|
| JP | 2011183056 | * | 9/2011 |
| JP | 2011-200533 A | | 10/2011 |
| JP | 2011200533 | * | 10/2011 |
| JP | 2014-087700 A | | 5/2014 |
| JP | 2016-083021 A | | 5/2016 |
| WO | 2017/006579 A1 | | 1/2017 |

OTHER PUBLICATIONS

The partial supplementary European search report issued by the European Patent Office dated Feb. 9, 2022, which corresponds to European Patent Application No. 19910472.0-1126 and is related to U.S. Appl. No. 17/347,246.
International Search Report issued in PCT/JP2019/049778; dated Mar. 10, 2020.
International Preliminary Report on Patentability and Written Opinion issued in PCT/JP2019/049778; dated Jun. 16, 2021.
The extended European search report issued by the European Patent Office dated Jun. 7, 2022, which corresponds to European Patent Application No. 19910472.0-1126 and is related to U.S. Appl. No. 17/347,246.

* cited by examiner

ULTRASOUND SYSTEM AND METHOD OF CONTROLLING ULTRASOUND SYSTEM

CROSS-REFERENCE TO RELATED APPLICATIONS

This application is a Continuation of PCT International Application No. PCT/JP2019/049778 filed on Dec. 19, 2019, which claims priority under 35 U.S.C. § 119(a) to Japanese Patent Application No. 2019-004702 filed on Jan. 15, 2019. The above application is hereby expressly incorporated by reference, in its entirety, into the present application.

BACKGROUND OF THE INVENTION

1. Field of the Invention

The present invention relates to an ultrasound system and a method of controlling an ultrasound system, and in particular, to an ultrasound system that displays an ultrasound image on a head-mounted display and a method of controlling an ultrasound system.

2. Description of the Related Art

Hitherto, in a medical field, an ultrasound diagnostic apparatus using an ultrasound image has come into practical use. In general, this kind of ultrasound diagnostic apparatus has an ultrasound probe that incorporates a transducer array, and an apparatus body connected to the ultrasound probe. The ultrasound probe transmits ultrasonic waves toward a subject and receives ultrasound echoes from the subject, and the apparatus body electrically processes reception signals to generate an ultrasound image.

In such an ultrasound diagnostic apparatus, usually, a monitor on which the ultrasound image is often disposed at a position away from the ultrasound probe, such as a bedside, and thus, a user needs to alternately move a line of sight between the ultrasound probe at hand and the monitor. To reduce the movement of the line of sight of the user, for example, an ultrasound diagnostic apparatus comprising a so-called head-mounted display as disclosed in JP2011-200533A has been developed. In the ultrasound diagnostic apparatus of JP2011-200533A, an ultrasound image is displayed on the head-mounted display.

SUMMARY OF THE INVENTION

Here, the ultrasound diagnostic apparatus of JP2011-200533A has a configuration in which the ultrasound probe and the head-mounted display are connected to a so-called stationary body, and is used for a user in a state of being provided at a position away from the ultrasound probe, such as a bedside. For this reason, in the ultrasound diagnostic apparatus of JP2011-200533A, while the head-mounted display is provided to achieve improvement of operability in ultrasonography, there is difficulty in mobility in a case where the user performs ultrasonography, such as limitation on a place where ultrasonography is performed.

The invention has been accomplished to solve the problem in the related art, and an object of the invention is to provide an ultrasound system and a method of controlling an ultrasound system capable of improving operability in a case where a user performs ultrasonography and improving mobility.

To achieve the above-described object, the invention provides an ultrasound system in which a mobile information terminal is connected to an ultrasound probe and a head-mounted display having a head-mounted display-side display unit. The ultrasound probe includes a transducer array, a transmission and reception unit that transmits an ultrasonic wave from the transducer array and generates a sound ray signal based on a reception signal acquired by the transducer array, an image information data generation unit that generates image information data based on the sound ray signal generated by the transmission and reception unit, and a probe-side wireless communication unit that transmits the image information data to the mobile information terminal in a wireless manner. The mobile information terminal includes a mobile information terminal-side display unit, an input unit that includes a touch sensor disposed to be superimposed on the mobile information terminal-side display unit and is used by a user to perform an input operation, an operation image generation unit that generates an operation image that is displayed on the mobile information terminal-side display unit and is used by the user to perform the input operation through the touch sensor, a head-mounted display data generation unit that generates head-mounted display data having a display format for the head-mounted display-side display unit based on the image information data transmitted from the ultrasound probe in a wireless manner, and a terminal-side wireless communication unit that transmits the head-mounted display data generated by the head-mounted display data generation unit to the head-mounted display in a wireless manner. The head-mounted display displays a head-mounted display ultrasound image on the head-mounted display-side display unit based on the head-mounted display data transmitted from the mobile information terminal in a wireless manner.

It is preferable that the head-mounted display has an ultrasound image display mode in which the head-mounted display ultrasound image is displayed on the head-mounted display-side display unit and an ultrasound image non-display mode in which the head-mounted display ultrasound image is not displayed on the head-mounted display-side display unit.

In this case, it is preferable that the mobile information terminal displays the operation image and a terminal ultrasound image based on the image information data generated by the image information data generation unit on the mobile information terminal-side display unit in a case where the head-mounted display is in the ultrasound image non-display mode.

The head-mounted display may select any of the ultrasound image display mode and the ultrasound image non-display mode in compliance with an input operation of the user on the operation image through the touch sensor of the mobile information terminal.

Alternatively, the head-mounted display may further include a microphone, the mobile information terminal may further include a voice analysis unit that analyzes voice of the user acquired by the microphone of the head-mounted display, and the head-mounted display may select any of the ultrasound image display mode and the ultrasound image non-display mode in compliance with the voice of the user acquired by the microphone and analyzed by the voice analysis unit.

Alternatively, the head-mounted display may further include an eye camera unit that generates an eye image obtained by imaging eyes of the user, the mobile information terminal may further include an eye movement detection unit that detects movement of the eyes of the user based on the eye image generated by the eye camera unit, and the head-mounted display may select any of the ultrasound image display mode and the ultrasound image non-display mode in compliance with the movement of the eyes of the user detected by the eye movement detection unit.

Alternatively, the head-mounted display may further include a disposition position sensor that detects whether or not the head-mounted display-side display unit is positioned at a given disposition position with respect to a head of the user, and the head-mounted display may select the ultrasound image display mode in a case where the disposition position sensor detects that the head-mounted display-side display unit is positioned at the given disposition position, and may select the ultrasound image non-display mode in a case where the disposition position sensor detects that the head-mounted display-side display unit is not positioned at the given disposition position.

In this case, the head-mounted display may further include a display movement unit that moves the head-mounted display-side display unit between the given disposition position and a given standby position different from the given disposition position.

Here, the head-mounted display may further include a microphone, the mobile information terminal may further include a voice analysis unit that analyzes voice of the user acquired by the microphone of the head-mounted display, and the display movement unit of the head-mounted display may move the head-mounted display-side display unit in compliance with the voice of the user acquired by the microphone and analyzed by the voice analysis unit.

Alternatively, the head-mounted display may further include an eye camera unit that generates an eye image obtained by imaging eyes of the user, the mobile information terminal may further include an eye movement detection unit that detects movement of the eyes of the user based on the eye image generated by the eye camera unit, and the display movement unit of the head-mounted display may move the head-mounted display-side display unit in compliance with the movement of the eyes of the user detected by the eye movement detection unit.

The head-mounted display data may include data corresponding to the head-mounted display ultrasound image and the operation image generated by the operation image generation unit, and the head-mounted display may display the head-mounted display ultrasound image and a head-mounted display operation image identical to the operation image displayed on the mobile information terminal-side display unit on the head-mounted display-side display unit based on the head-mounted display data.

Alternatively, the head-mounted display may further include a view camera unit that generates a view image obtained by imaging a field of view in front of the user, the mobile information terminal may further include a view image analysis unit that performs image analysis on the view image generated by the view camera unit, and the head-mounted display data generation unit may generate the head-mounted display data by adding a result of the image analysis of the view image analysis unit.

In this case, the view image analysis unit may detect a screen of the mobile information terminal-side display unit shown in the view image generated by the view camera unit, the head-mounted display data may include data corresponding to the head-mounted display ultrasound image and the screen of the mobile information terminal-side display unit detected by the view image analysis unit, and the head-mounted display may display the head-mounted display ultrasound image and a terminal screen image representing the screen of the mobile information terminal-side display unit detected by the view image analysis unit on the head-mounted display-side display unit based on the head-mounted display data.

The view image analysis unit may calculate a distance between the ultrasound probe and the view camera unit based on the view image generated by the view camera unit, the head-mounted display data generation unit may set a size of a display region where the head-mounted display ultrasound image is displayed in the head-mounted display-side display unit, based on the distance calculated by the view image analysis unit to generate the head-mounted display data, and the head-mounted display may display the head-mounted display ultrasound image on the head-mounted display-side display unit based on the head-mounted display data with the size of the display region set by the head-mounted display data generation unit.

It is preferable that a wireless communication system between the mobile information terminal and the ultrasound probe is different from a wireless communication system between the mobile information terminal and the head-mounted display.

In this case, it is preferable that a frequency range in wireless communication between the mobile information terminal and the ultrasound probe is different from a frequency range in wireless communication between the mobile information terminal and the head-mounted display.

It is preferable that the mobile information terminal further includes a safety evaluation index calculation unit that calculates a safety evaluation index based on conditions of transmission and reception of the ultrasonic wave in the ultrasound probe and displays the safety evaluation index on the mobile information terminal-side display unit.

It is preferable that the image information data is a signal obtained by executing attenuation correction and envelope detection processing depending on a depth of a reflection position of the ultrasonic wave on the sound ray signal generated by the transmission and reception unit.

Alternatively, the image information data may be an ultrasound image signal obtained by executing attenuation correction and envelope detection processing depending on a reflection position of the ultrasonic wave on the sound ray signal generated by the transmission and reception unit and converting the sound ray signal in compliance with a given image display system.

It is preferable that the transmission and reception unit includes a transmission unit that directs the transducer array to transmit the ultrasonic wave, and a reception unit that generates the sound ray signal based on a reception signal acquired by the transducer array.

The invention provides a method of controlling an ultrasound system in which a mobile information terminal is connected to an ultrasound probe and a head-mounted display having a head-mounted display-side display unit. The method comprises generating a sound ray signal by directing a transducer array of the ultrasound probe to transmit and receive an ultrasonic wave based on an input operation through an input unit of the mobile information terminal, generating image information data based on the generated sound ray signal, transmitting the generated image information data from the ultrasound probe to the mobile information terminal in a wireless manner, generating an operation image that is used by a user to perform an input operation, displaying the operation image on a display unit of the mobile information terminal, generating head-mounted display data having a display format for the head-mounted display-side display unit based on the image information data transmitted from the ultrasound probe in a wireless manner, transmitting the generated head-mounted display data from the mobile information terminal to the head-mounted display in a wireless manner, and displaying the head-mounted display ultrasound image on the head-mounted display-side display unit based on the head-mounted display data.

A mobile information terminal includes a display unit, an input unit that includes a touch sensor disposed to be superimposed on the display unit and is used by a user to perform an input operation, an operation image generation unit that generates an operation image that is displayed on the display unit and is used by the user to perform the input operation through the touch sensor, a head-mounted display data generation unit that generates head-mounted display data having a display format for the head-mounted display-side display unit based on image information data transmitted from an ultrasound probe in a wireless manner, and a terminal-side wireless communication unit that transmits the head-mounted display data generated by the head-mounted display data generation unit to a head-mounted display in a wireless manner. The head-mounted display-side display unit displays a head-mounted display ultrasound image based on the head-mounted display data transmitted from the mobile information terminal in a wireless manner. Therefore, it is possible to improve operability in a case where the user performs ultrasonography, and to improve mobility.

DESCRIPTION OF THE PREFERRED EMBODIMENTS

Hereinafter, embodiments of the invention will be described referring to the accompanying drawings.

The description of components described below is provided based on a representative embodiment of the invention, but the invention is not limited to such an embodiment.

In the specification, a numerical range represented using "to" means a range including numerical values before and after "to" as a lower limit value and an upper limit value.

In the specification, the terms "same" and "identical" include an error range allowed in the technical field. In the specification, in a case of referring to "all", "any", "whole surface", or the like, the term includes an error range generally allowed in the technical field in addition to a case of 100%, and includes, for example, a case of equal to or more than 99%, a case of equal to or more than 95%, or a case of equal to or more than 90%.

Embodiment 1

Figure 1:
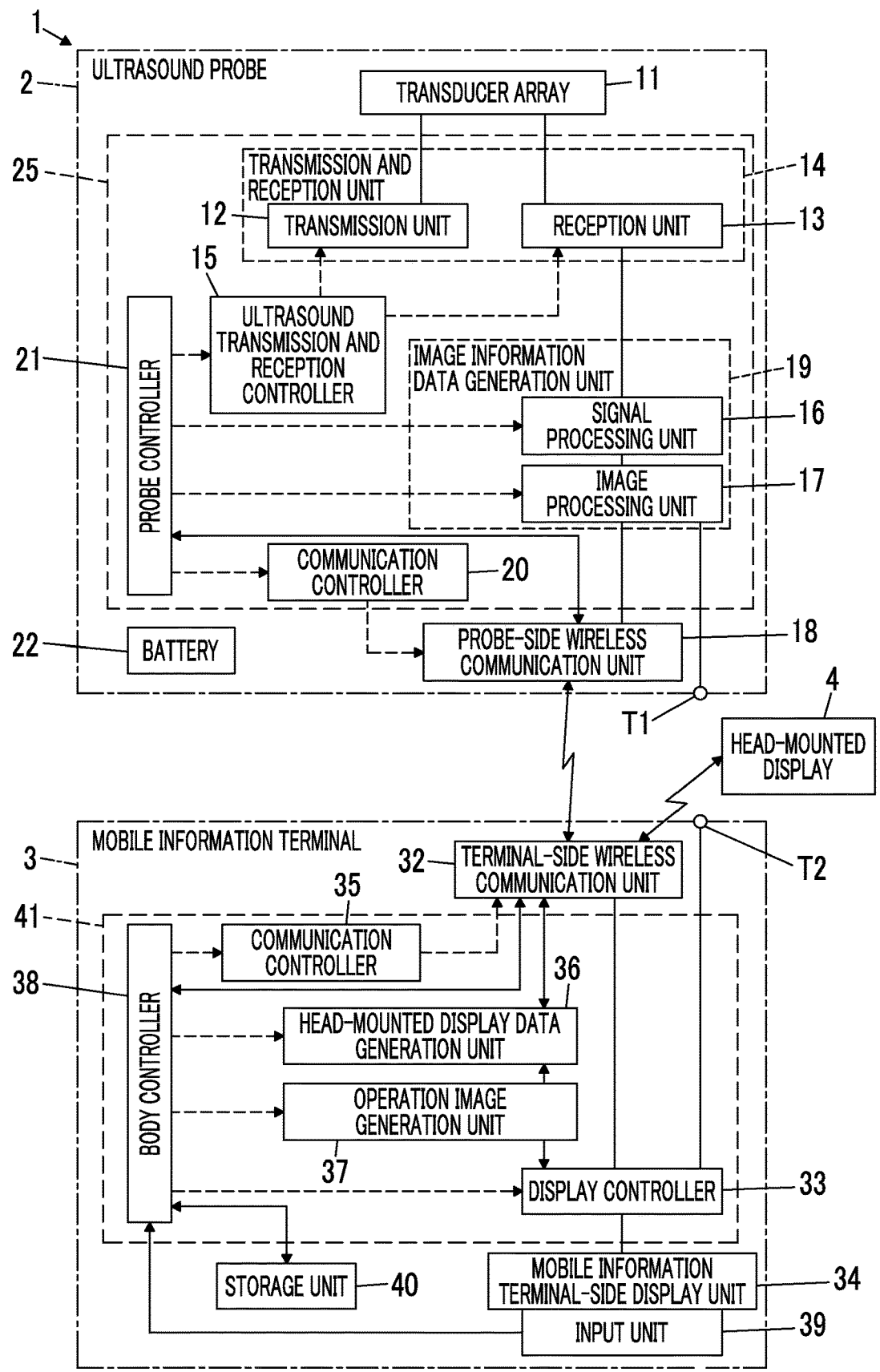
FIG. 1 is a block diagram showing the configuration of an ultrasound system according to Embodiment 1 of the invention.

FIG. 1 shows the configuration of an ultrasound system 1 according to Embodiment 1 of the invention. The ultrasound system 1 comprises an ultrasound probe 2, a mobile information terminal 3, and a head-mounted display 4. The ultrasound probe 2 and the head-mounted display 4 are connected to the mobile information terminal 3 by wireless communication. The head-mounted display 4 is a display device that is mounted on a head of a user and is viewed by the user who mounts the head-mounted display 4, an ultrasound image and the like are transmitted from the mobile information terminal 3 to the head-mounted display 4 in a wireless manner, and the transmitted ultrasound image and the like are displayed on the head-mounted display 4.

As shown in FIG. 1, the ultrasound probe 2 comprises a transducer array 11, and a transmission unit 12 and a reception unit 13 are connected to the transducer array 11. The transmission unit 12 and the reception unit 13 form a transmission and reception unit 14, and ultrasound transmission and reception controller 15 is connected to the transmission unit 12 and the reception unit 13. A signal processing unit 16 and an image processing unit 17 are sequentially connected to the reception unit 13. Here, the signal processing unit 16 and the image processing unit 17 constitute an image information data generation unit 19. A probe-side wireless communication unit 18 and a probe-side connection terminal T1 are connected to the image processing unit 17, and a communication controller 20 is connected to the probe-side wireless communication unit 18.

A probe controller 21 is connected to the ultrasound transmission and reception controller 15, the signal processing unit 16, the image processing unit 17, the probe-side wireless communication unit 18, and the communication controller 20. Here, the probe-side wireless communication unit 18 and the probe controller 21 are connected to transfer information in two directions. The ultrasound probe 2 incorporates the battery 22.

The transmission and reception unit 14, the ultrasound transmission and reception controller 15, the image information data generation unit 19, the communication controller 20, and the probe controller 21 constitute a probe processor 25.

The mobile information terminal 3 has a terminal-side wireless communication unit 32, and a display controller 33 is connected to the terminal-side wireless communication unit 32. A communication controller 35 and a head-mounted display data generation unit 36 are connected to the terminal-side wireless communication unit 32. The terminal-side wireless communication unit 32 and the head-mounted display data generation unit 36 are connected to transfer information in two directions. An operation image generation unit 37 is connected to the head-mounted display data generation unit 36, and the operation image generation unit 37 is connected to the display controller 33. A terminal-side connection terminal T2 and a mobile information terminal-side display unit 34 are connected to the display controller 33. An input unit 39 is disposed to be superimposed on the mobile information terminal-side display unit 34.

A body controller 38 is connected to the display controller 33, the communication controller 35, the head-mounted display data generation unit 36, the operation image generation unit 37, and the input unit 39, and a storage unit 40 is connected to the body controller 38. Here, the terminal-side wireless communication unit 32 and the body controller 38 are connected to transfer information in two directions. The body controller 38 and the storage unit 40 are connected to transfer information in two directions.

The display controller 33, the communication controller 35, the head-mounted display data generation unit 36, the operation image generation unit 37, and the body controller 38 constitute a terminal processor 41.

The transducer array 11 of the ultrasound probe 2 has a plurality of ultrasound transducers arranged in a one-dimensional or two-dimensional manner. Each transducer transmits an ultrasonic wave in response to a drive signal supplied from the transmission unit 12, receives a reflected wave from a subject, and outputs an analog reception signal. Each ultrasound transducer is constituted using elements in which electrodes are formed at both ends of a piezoelectric body made of, for example, piezoelectric ceramic represented by lead zirconatetitanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception controller 15 performs control such that the transmission unit 12 and the reception unit 13 of the transmission and reception unit 14 transmit an ultrasonic beam and receive an ultrasound echo based on an examination mode and a scanning system instructed from the probe controller 21. Here, the examination mode indicates any of examination modes usable in an ultrasound diagnostic apparatus, such as a brightness (B) mode, a motion (M) mode, a color Doppler (CD) mode, a power Doppler (PD) mode, a pulsed Doppler (PW) mode, and a continuous-wave Doppler (CW) mode, and the scanning system indicates any of an electronic sector scanning system, an electronic linear scanning system, and an electronic convex scanning system.

The transmission unit 12 of the transmission and reception unit 14 includes, for example, a plurality of pulse generators, and adjusts a delay amount of each drive signal based on a transmission delay pattern selected in response to a control signal from the ultrasound transmission and reception controller 15 such that the ultrasonic waves transmitted from a plurality of transducers of the transducer array 11 form an ultrasonic beam, and supplies the drive signals to a plurality of transducers. In this way, in a case where a pulsed or continuous-wave voltage is applied to the electrodes of each transducer of the transducer array 11, the piezoelectric body expands and contracts to generate a pulsed or continuous-wave ultrasonic wave from each transducer. An ultrasonic beam with a narrowed focus on a certain scanning line is formed from a combined wave of the ultrasonic waves.

The transmitted ultrasonic beam is reflected by, for example, a target, such as a part of the subject, and propagates as a so-called ultrasound echo toward the transducer array 11. The ultrasound echo propagating toward the transducer array 11 is received by each transducer constituting the transducer array 11. In this case, each transducer constituting the transducer array 11 expands and contracts with reception of the propagating ultrasound echo to generate an electrical signal, and outputs the electrical signal to the reception unit 13.

Figure 2:
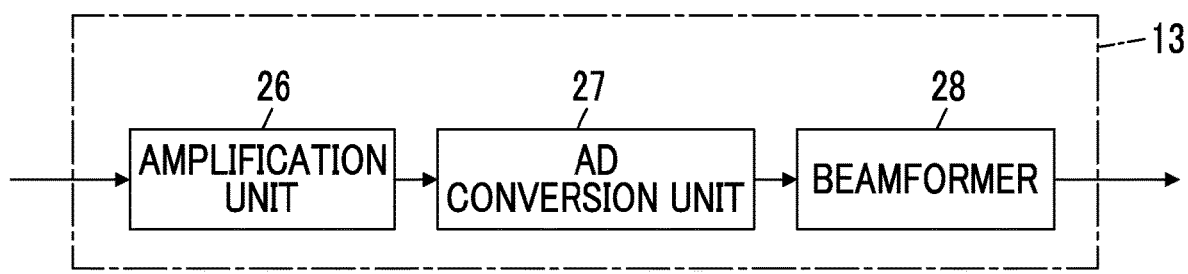
FIG. 2 is a block diagram showing the configuration of a reception unit in Embodiment 1 of the invention.

The reception unit 13 of the transmission and reception unit 14 executes processing of the reception signal output from the transducer array 11 in response to a control signal from the ultrasound transmission and reception controller 15. As shown in FIG. 2, the reception unit 13 has a configuration in which an amplification unit 26, an analog-digital (AD) conversion unit 27, and a beamformer 28 are connected in series. The amplification unit 26 amplifies the reception signal that is an analog signal input from each ultrasound transducer constituting the transducer array 11 and transmits the amplified reception signal to the AD conversion unit 27. The AD conversion unit 27 converts the analog reception signal transmitted from the amplification unit 26 into a digital signal to acquire reception data and sends the reception data to the beamformer 28. The beamformer 28 executes reception focus processing of giving a delay to each piece of data compliant with a set sound speed based on a reception delay pattern selected in response to a control signal from the ultrasound transmission and reception controller 15 and performing addition (phasing addition). With the reception focus processing, a sound ray signal in which a focus of the ultrasound echo is narrowed on a certain scanning line is generated.

The image information data generation unit 19 of the probe processor 25 generates image information data based on the sound ray signal generated by the beamformer 28 of the reception unit 13.

Here, the signal processing unit 16 of the image information data generation unit 19 performs correction of attenuation on the sound ray signal generated by the beamformer 28 of the reception unit 13 due to a propagation distance depending on a depth of a position where the ultrasonic wave is reflected, and then, executes envelope detection processing to generate a signal representing tomographic image information regarding a tissue in the subject.

The image processing unit 17 of the image information data generation unit 19 raster-converts the signal generated by the signal processing unit 16 into an image signal compliant with a normal television signal scanning system, generates an ultrasound image signal by executing various kinds of necessary processing, such as brightness correction, gradation correction, sharpness correction, image size correction, refresh rate correction, scanning frequency correction, and color correction compliant with a display format for the mobile information terminal-side display unit 34, on the image signal generated in this manner, and then, sends the ultrasound image signal as image information data to the probe-side wireless communication unit 18 or the probe-side connection terminal T1.

The probe-side wireless communication unit 18 of the ultrasound probe 2 includes an antenna that performs transmission and reception of radio waves, and modulates a carrier based on the ultrasound image signals generated in the image information data generation unit 19 to generate transmission signals representing the ultrasound image signals. The probe-side wireless communication unit 18 supplies the transmission signals representing the ultrasound image signals generated in this manner to the antenna and transmits radio waves from the antenna, thereby sequentially the ultrasound image signals in a wireless manner. As a modulation system of the carrier, for example, amplitude shift keying (ASK), phase shift keying (PSK), quadrature phase shift keying (QPSK), 16 quadrature amplitude modulation (16QAM), or the like is used.

The probe-side wireless communication unit 18 receives a transmission signal representing probe control information for controlling the ultrasound probe 2 from the mobile information terminal 3 and sends the probe control information acquired by demodulating the received transmission signal to the probe controller 21. Though described below, the probe control information is input by the user through the input unit 39 of the mobile information terminal 3, for example.

The communication controller 20 of the probe processor 25 performs control such that the probe-side wireless communication unit 18 transmits the ultrasound image signals with transmission field intensity set by the probe controller 21. The communication controller 20 of the probe processor 25 performs control such that the probe-side wireless communication unit 18 receives the probe control information transmitted from the mobile information terminal 3 in a wireless manner.

The probe-side connection terminal T1 of the ultrasound probe 2 is a terminal that is used in a case where the ultrasound probe 2 and the mobile information terminal 3 are connected in a wired manner and information is transferred between the ultrasound probe 2 and the mobile information terminal 3 in two directions. In this case, for example, a connection cable that can transmit information is inserted into the probe-side connection terminal T1.

The probe controller 21 of the probe processor 25 performs control of each unit of the ultrasound probe 2 based on a program stored in advance and the like.

The battery 22 of the ultrasound probe 2 is incorporated in the ultrasound probe 2, and supplies electric power to each circuit of the ultrasound probe 2.

Although the probe processor 25 having the transmission unit 12, the reception unit 13, the ultrasound transmission and reception controller 15, the signal processing unit 16, the image processing unit 17, the communication controller 20, and the probe controller 21 the ultrasound probe 2 is constituted of a central processing unit (CPU) and a control program causing the CPU to execute various kinds of processing, the probe processor 25 may be constituted using a field programmable gate array (FPGA), a digital signal processor (DSP), an application specific integrated circuit (ASIC), or other integrated circuits (ICs) or may be constituted by combining the IC circuits. The transmission unit 12, the reception unit 13, the ultrasound transmission and reception controller 15, the signal processing unit 16, the image processing unit 17, the communication controller 20, and the probe controller 21 can also be constituted to be partially or wholly integrated into one CPU or the like.

The terminal-side wireless communication unit 32 of the mobile information terminal 3 includes an antenna that performs transmission and reception of radio waves, receives a the transmission signal representing the ultrasound image signal transmitted from the probe-side wireless communication unit 18 of the ultrasound probe 2, through the antenna, and sends the ultrasound image signal output by demodulating the received transmission signal to the display controller 33. The terminal-side wireless communication unit 32 generates the transmission signal representing the probe control information by modulating a carrier based on the probe control information for controlling the ultrasound probe 2 sent from the body controller 38 and transmits the generated transmission signal to the probe-side wireless communication unit 18 of the ultrasound probe 2 in a wireless manner.

As described below, the terminal-side wireless communication unit 32 generates transmission signal representing head-mounted display data by modulating a carrier based on head-mounted display data generated by the head-mounted display data generation unit 36 and transmits the generated transmission signal to the head-mounted display 4 in a wireless manner. As described below, the head-mounted display data includes a head-mounted display ultrasound image signal having a display format on the head-mounted display 4. The terminal-side wireless communication unit 32 generates a transmission signal representing head-mounted display control information for controlling the head-mounted display 4 sent from the body controller 38 and transmits the generated transmission signal to the head-mounted display 4 in a wireless manner.

Here, as a modulation system of the carrier in the terminal-side wireless communication unit 32, like the modulation system of the carrier in the probe-side wireless communication unit 18, ASK, PSK, QPSK, 16QAM, or the like is used.

The communication controller 35 of the terminal processor 41 performs control such that the terminal-side wireless communication unit 32 of the mobile information terminal 3 receives the transmission signal representing the ultrasound image signal from the probe-side wireless communication unit 18 of the ultrasound probe 2. The communication controller 35 of the terminal processor 41 performs control such that the terminal-side wireless communication unit 32 transmits data to the ultrasound probe 2 and the head-mounted display 4 with transmission field intensity set by the body controller 38 in a wireless manner.

The input unit 39 of the mobile information terminal 3 is provided for the user to perform an input operation, and includes a touch sensor disposed to be superimposed on the mobile information terminal-side display unit 34. For example, the probe control information for controlling the ultrasound probe 2 is input by the user through the input unit 39, the input probe control information is transmitted to the terminal-side wireless communication unit 32 to the ultrasound probe 2 through the body controller 38 of the terminal processor 41 in a wireless manner. For example, the head-mounted display control information for controlling the head-mounted display 4 is input by the user through the input unit 39, and the input head-mounted display control information is transmitted from the terminal-side wireless communication unit 32 to the head-mounted display 4 through the body controller 38 of the terminal processor 41.

The operation image generation unit 37 of the terminal processor 41 generates an operation image that is displayed on the mobile information terminal-side display unit 34 and is used by the user to perform an input operation through the touch sensor of the input unit 39. For example, as shown in FIG. 3, an operation image CS1 includes various operation buttons, such as a B mode button B1 for deciding the examination mode to the B mode in the ultrasound probe 2, and the user touches the operation buttons to input the probe control information, the head-mounted display control information, and the like through the touch sensor of the input unit 39.

Figure 3:
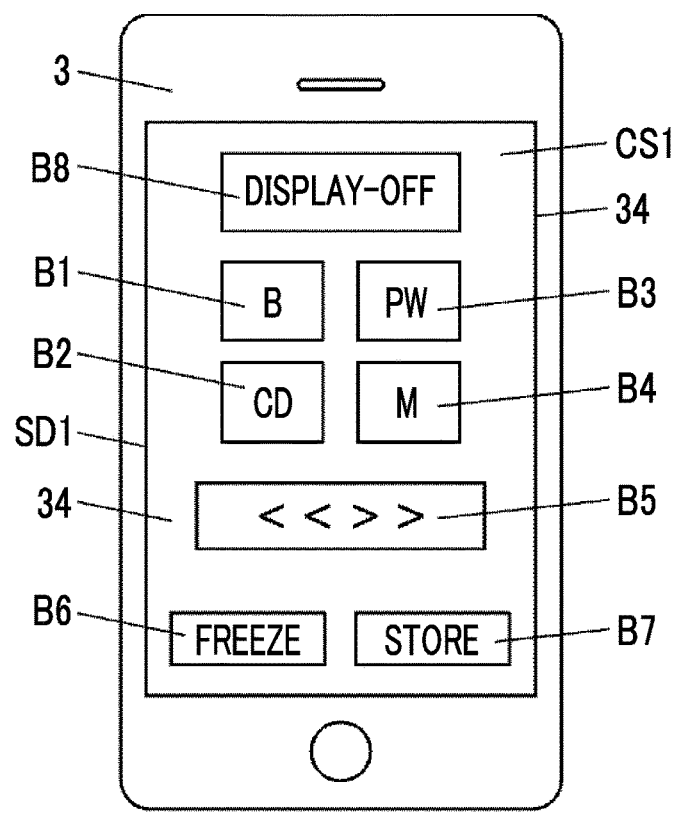
FIG. 3 is a diagram schematically showing an operation image displayed on a mobile information terminal in Embodiment 1 of the invention.

In an example shown in FIG. 3, the operation image CS1 includes, in addition to a B mode button B1, a CD mode button B2 for deciding the examination mode to the CD mode, a PW mode button B3 for deciding the examination mode to the PW mode, an M mode button B4 for deciding the examination mode to the M mode, a scroll button B5 for scroll display, a freeze button B6 for freeze display of the ultrasound image, a save button B7 for saving an ultrasound image, and a display-off button B8 for turning off the display of the ultrasound image on the head-mounted display 4 in a case where the ultrasound image is displayed on the head-mounted display 4.

The head-mounted display data generation unit 36 of the terminal processor 41 generates data corresponding to the head-mounted display ultrasound image that can be displayed on the head-mounted display 4 and the operation image CS1 as head-mounted display data having a display format for the head-mounted display 4 based on the ultrasound image signal output from the terminal-side wireless communication unit 32 and the operation image CS1 generated by the operation image generation unit 37. In this case, the head-mounted display data generation unit 36 generates an ultrasound image signal for the head-mounted display 4 as the data corresponding to the head-mounted display ultrasound image by executing various kinds of necessary image processing, such as brightness correction, gradation correction, sharpness correction, image size correction, refresh rate correction, scanning frequency correction, and color correction compliant with the display format for the head-mounted display 4, on the ultrasound image signal output from the terminal-side wireless communication unit 32.

Under the control of the body controller 38, the display controller 33 of the terminal processor 41 executes predetermined processing on the ultrasound image signal output from the terminal-side wireless communication unit 32 and the operation image CS1 generated by the operation image generation unit 37, and displays the operation image CS1 and a terminal ultrasound image that has the display format for the mobile information terminal-side display unit 34 and can be displayed on the mobile information terminal-side display unit 34, on the mobile information terminal-side display unit 34.

The mobile information terminal-side display unit 34 displays the terminal ultrasound image and the operation image CS1 under the control of the display controller 33. The mobile information terminal-side display unit 34 includes, for example, a display device, such as a liquid crystal display (LCD) or an organic electroluminescence display (organic EL display).

Like the probe-side connection terminal T1 of the ultrasound probe 2, the terminal-side connection terminal T2 of the mobile information terminal 3 is a terminal that is used in a case where the ultrasound probe 2 and the mobile information terminal 3 are connected in a wired manner and information is transferred between the ultrasound probe 2 and the mobile information terminal 3 in two directions. For example, the terminal-side connection terminal T2 is connected to the other end of the connection cable one end of which is connected to the probe-side connection terminal T1.

The storage unit 40 of the mobile information terminal 3 stores an operation program and the like of the mobile information terminal 3, and a flash memory, a random access memory (RAM), a secure digital card (SD card), a solid state drive (SSD), or the like can be used as the storage unit 40.

The terminal processor 41 having the display controller 33, the communication controller 35, the head-mounted display data generation unit 36, the operation image generation unit 37, and the body controller 38 of the mobile information terminal 3 is constituted of a CPU and a control program causing the CPU to execute various kinds of processing, the terminal processor 41 may be constituted using an FPGA, a DSP, an ASIC, a GPU, or other ICs or may be constituted by combining the ICs. The display controller 33, the communication controller 35, the head-mounted display data generation unit 36, the operation image generation unit 37, and the body controller 38 can also be constituted to be partially or wholly integrated into one CPU or the like.

Figure 4:
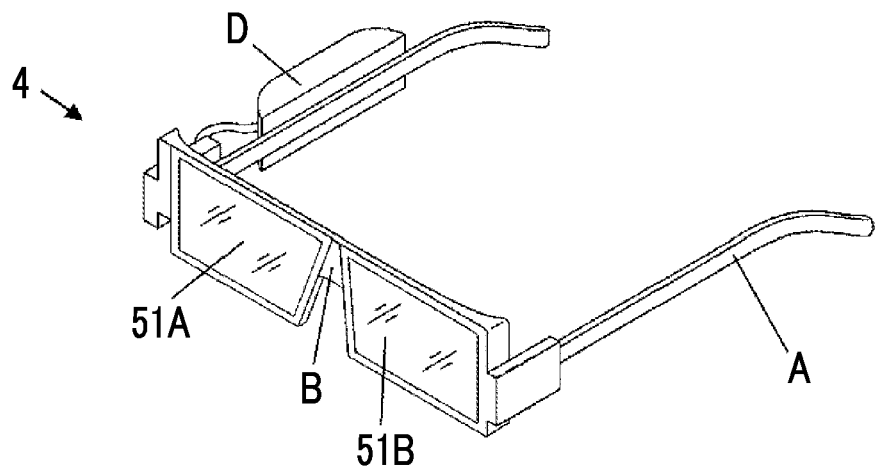
FIG. 4 is a diagram schematically showing a head-mounted display in Embodiment 1 of the invention.

The head-mounted display 4 of the ultrasound system 1 is a display device that is mounted on the head of the user and is viewed by the user who mounts the head-mounted display 4, and as shown in FIG. 4, has a shape of so-called spectacles. The head-mounted display 4 comprises two display units 51A and 51B, and the two display units 51A and 51B are connected by a bridge portion B, and temple portions A are connected to end portions of the two display units 51A and 51B, respectively. For example, the bridge portion B is placed and fixed on a nose of the user, and the two temple portions A are placed and fixed on both ears of the user, whereby the head-mounted display 4 is fixed to the head of the subject. In this case, the two display units 51A and 51B face right and left eyes of the user, respectively.

An accommodation portion D where various circuits necessary for the operation of the head-mounted display 4, a battery, and the like are accommodated is disposed in the temple portion A connected to the right display unit 51A.

Figure 5:
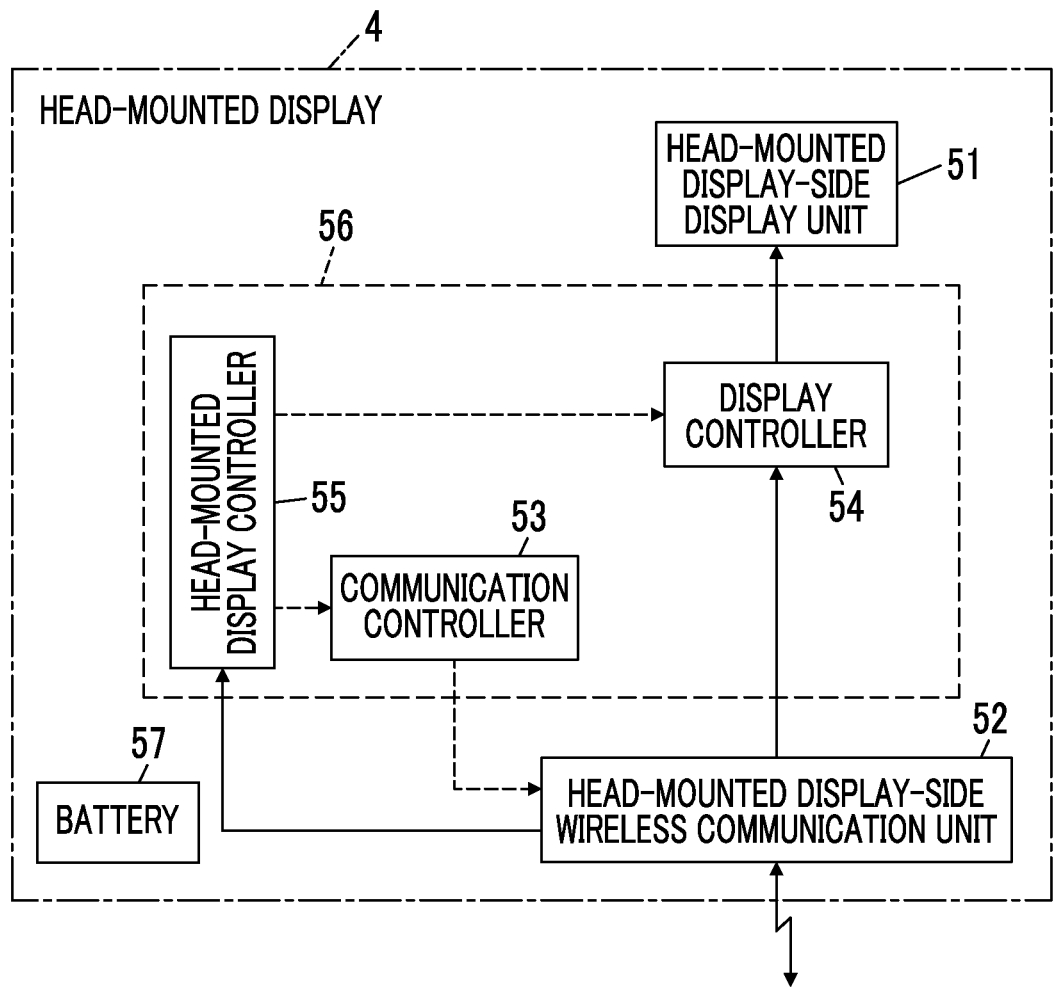
FIG. 5 is a block diagram showing the configuration of the head-mounted display in Embodiment 1 of the invention.

FIG. 5 shows the configuration of the head-mounted display 4. The head-mounted display 4 has a head-mounted display-side wireless communication unit 52, and a communication controller 53, a display controller 54, and a head-mounted display controller 55 are connected to the head-mounted display-side wireless communication unit 52. A head-mounted display-side display unit 51 is connected to the display controller 54.

For description, the two display units 51A and 51B in FIG. 4 are collectively referred to as the head-mounted display-side display unit 51.

The communication controller 53, the display controller 54, and the head-mounted display controller 55 constitute a head-mounted display processor 56. A battery 57 is incorporated in the head-mounted display 4. The head-mounted display-side wireless communication unit 52, the head-mounted display processor 56, and the battery 57 are accommodated in the accommodation portion D of the head-mounted display 4.

The head-mounted display-side wireless communication unit 52 of the head-mounted display 4 includes an antenna that performs transmission and reception of radio waves, receives the head-mounted display data from the mobile information terminal 3, and sends the received head-mounted display data to the display controller 54. The head-mounted display-side wireless communication unit 52 receives the head-mounted display control information for controlling the head-mounted display 4 from the mobile information terminal 3 and outputs the received head-mounted display control information to the head-mounted display controller 55.

The head-mounted display-side display unit 51 of the head-mounted display 4 has transmittance to secure the field of view of the user in a state in which the user mounts the head-mounted display 4. The head-mounted display-side display unit 51 is a display that displays the ultrasound image and the like. The head-mounted display-side display unit 51 has such a configuration, and can thus display the ultrasound image and the like transmitted from the mobile information terminal 3.

Figure 6:
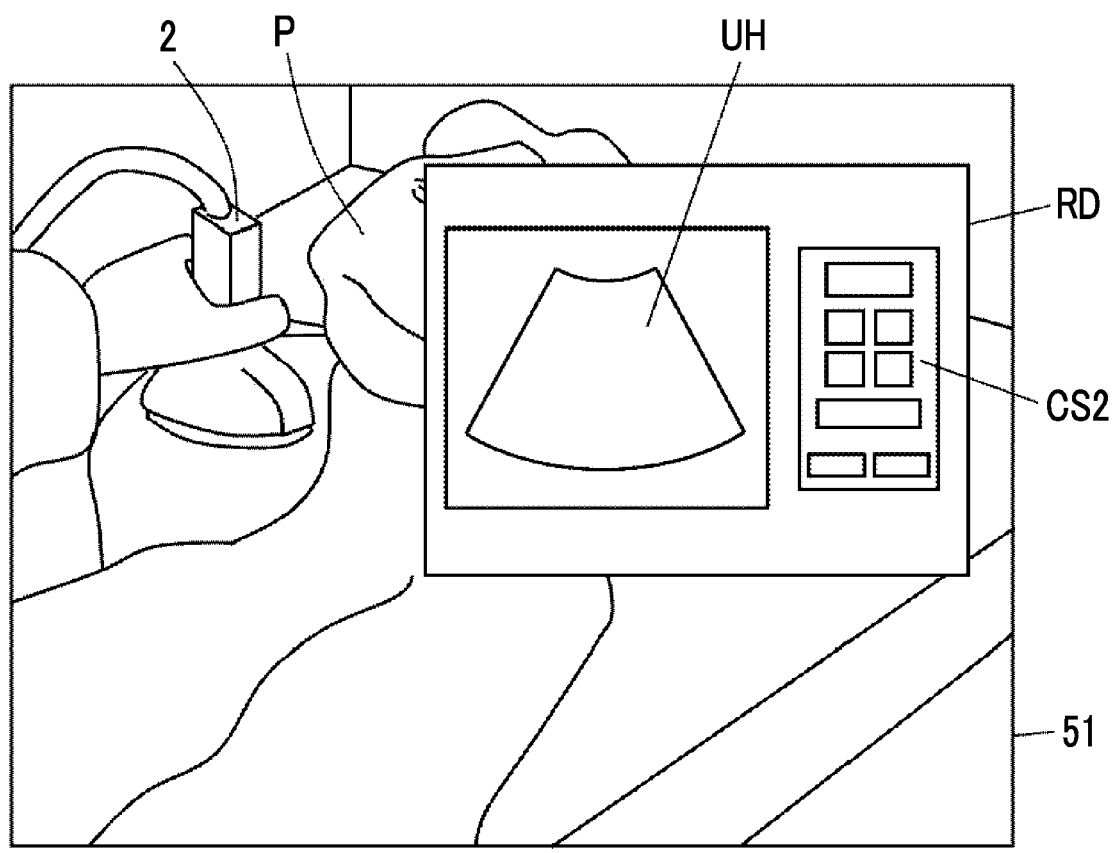
FIG. 6 is a diagram schematically showing a head-mounted display ultrasound image and a head-mounted display operation image displayed on a head-mounted display-side display unit in Embodiment 1 of the invention.

As shown in FIG. 6, the display controller 54 of the head-mounted display processor 56 displays a head-mounted display operation image CS2 and a head-mounted display ultrasound image UH compliant with a display format of the head-mounted display-side display unit 51 on the head-mounted display-side display unit 51 based on the head-mounted display data transmitted from the mobile information terminal 3 in a wireless manner under the control of the head-mounted display controller 55. Here, the head-mounted display operation image CS2 displayed on the head-mounted display-side display unit 51 is the same as the operation image CS1 displayed on the mobile information terminal-side display unit 34.

In this case, for example, as shown in FIG. 6, a display region RD where the head-mounted display ultrasound image UH and the head-mounted display operation image CS2 are displayed is displayed on the head-mounted display-side display unit 51, and the head-mounted display ultrasound image UH and the head-mounted display operation image CS2 are displayed in the display region RD. The head-mounted display-side display unit 51 has transmittance, and as shown in FIG. 6, the user can view a subject P, the ultrasound probe 2, and the like through the head-mounted display-side display unit 51.

The head-mounted display controller 55 of the head-mounted display processor 56 performs control of each unit of the head-mounted display 4 based on a program stored in advance, the head-mounted display control information transmitted from the mobile information terminal 3 in a wireless manner, and the like.

Here, under the control of the head-mounted display controller 55, the head-mounted display 4 has an ultrasound image display mode in which the head-mounted display ultrasound image UH is displayed on the head-mounted display-side display unit 51 and an ultrasound image non-display mode in which the head-mounted display ultrasound image UH is not displayed on the head-mounted display-side display unit 51. For example, in compliance with the head-mounted display control information input by the user through the input unit 39 of the mobile information terminal 3, the head-mounted display controller 55 selects whether the head-mounted display 4 is set to the ultrasound image displayed mode or the ultrasound image non-display mode.

The battery 57 of the head-mounted display 4 is incorporated in the head-mounted display 4, and supplies electric power to each circuit of the head-mounted display 4.

Although the head-mounted display processor 56 having the communication controller 53, the display controller 54, and the head-mounted display controller 55 is constituted of a CPU and a control program causing the CPU to execute various kinds of processing, the head-mounted display processor 56 may be constituted using an FPGA, a DSP, an ASIC, a GPU, or other ICs or may be constituted by combining the ICs. The communication controller 53, the display controller 54, and the head-mounted display controller 55 can also be constituted to be partially or wholly integrated into one CPU or the like.

Next, the operation of the ultrasound system 1 according to Embodiment 1 of the invention will be described. Here, when ultrasonography is started, the head-mounted display 4 is set to the ultrasound image non-display mode between the ultrasound image display mode and the ultrasound image non-display mode.

First, in the mobile information terminal 3, the operation image generation unit 37 of the terminal processor 41 generates the operation image CS1 that is displayed on the mobile information terminal-side display unit 34 and is used by the user to perform an input operation through the touch sensor of the input unit 39. As shown in FIG. 3, the operation image CS1 can include buttons for operating the ultrasound probe 2, such as the B mode button B1 and the CD mode button B2, buttons for operating the head-mounted display 4, such as the scroll button B5 and the display-off button B8. The operation image CS1 generated in this manner is displayed on the mobile information terminal-side display unit 34 as shown in FIG. 3 under the control of the display controller 33 of the mobile information terminal 3.

Next, the examination mode for use in ultrasonography is input as the probe control information by the user through the touch sensor of the input unit 39 in compliance with the operation image CS1 displayed on the mobile information terminal-side display unit 34. In this case, for example, the user touches the B mode button B1 of the operation image CS1 shown in FIG. 3 to input the probe control information indicating that the B mode is used as the examination mode. Hereinafter, for description, it is assumed that the B mode is used as the examination mode.

In this manner, in a case where the probe control information indicating that the B mode is used as the examination mode is input by the user, the probe control information input by the user is sent to the terminal-side wireless communication unit 32 of the mobile information terminal 3 through the body controller 38 of the terminal processor 41, and is then transmitted from the terminal-side wireless communication unit 32 to the ultrasound probe 2 in a wireless manner. The probe control information transmitted from the terminal-side wireless communication unit 32 in a wireless manner is received by the probe-side wireless communication unit 18, is sent to the probe controller 21, and is then sent from the probe controller 21 to the ultrasound transmission and reception controller 15, the signal processing unit 16, and the image processing unit 17. With this, the examination mode for use in ultrasonography is set to the B mode.

The ultrasound transmission and reception controller 15 of the probe processor 25 performs control such that the transmission and reception unit 14 performs transmission and reception of ultrasonic waves in the transducer array 11 based on the probe control information sent from the probe controller 21 indicating that the B mode is used as the examination mode. In this case, first, ultrasonic beams are transmitted from a plurality of ultrasound transducers of the transducer array 11 into the subject in response to the drive signals from the transmission unit 12 of the transmission and reception unit 14 under the control of the ultrasound transmission and reception controller 15. An ultrasound echo from the subject based on the transmitted ultrasonic beam is received by each ultrasound transducer, the reception signal that is an analog signal is output to the reception unit 13, is amplified by the amplification unit 26, and is AD converted by the AD conversion unit 27, and reception data is acquired. The beamformer 28 executes the reception focus processing on the reception data to generate a sound ray signal.

The signal processing unit 16 of the image information data generation unit 19 executes predetermined signal processing on the sound ray signal generated by the beamformer 28 of the reception unit 13 to generate a signal representing a tomographic image of a tissue in the subject. In this case, the signal processing unit 16 generates the signal representing the tomographic image based on information representing the examination mode sent from the probe controller 21, that is, the probe control information indicating that the B mode is used as the examination mode.

The image processing unit 17 raster-converts the signal generated by the signal processing unit 16 in this manner into an image signal compliant with a normal television signal scanning system, and executes various kinds of necessary processing, such as various kinds of necessary processing, such as brightness correction, gradation correction, sharpness correction, image size correction, refresh rate correction, scanning frequency correction, and color correction compliant with the display format for the mobile information terminal-side display unit 34, on the converted image signal to generate an ultrasound image signal as image information data.

The ultrasound image signal generated by the image processing unit 17 is transmitted to the terminal-side wireless communication unit 32 of the mobile information terminal 3 through the probe-side wireless communication unit 18 in a wireless manner, and is then sent from the terminal-side wireless communication unit 32 to the display controller 33 and the head-mounted display data generation unit 36.

The ultrasound image signal sent from the terminal-side wireless communication unit 32 to the display controller 33 is displayed on the mobile information terminal-side display unit 34 as a terminal ultrasound image compliant with the display format for the mobile information terminal-side display unit 34 under the control of the display controller 33. Though not shown, in this case, the display of the operation image CS1 on the mobile information terminal-side display unit 34 is switched to the display of the terminal ultrasound image.

Here, the user can input the head-mounted display control information indicating that the ultrasound image is to be displayed on the head-mounted display-side display unit 51, through the touch sensor of the input unit 39 in a case where the terminal ultrasound image is to be displayed on the mobile information terminal-side display unit 34. For example, a display-on button (not shown) for giving an instruction indicating that the ultrasound image is to be displayed on the head-mounted display-side display unit 51 is displayed on the mobile information terminal-side display unit 34, and the user touches the displayed display-on button through the touch sensor of the input unit 39 to input the head-mounted display control information indicating the ultrasound image is to be displayed on the head-mounted display-side display unit 51. The head-mounted display control information input in this manner is sent to the body controller 38, and is then sent from the body controller 38 to the head-mounted display data generation unit 36. In this case, the display of the terminal ultrasound image on the mobile information terminal-side display unit 34 is switched to the display of the operation image CS1.

The head-mounted display control information input by the user is transmitted from the terminal-side wireless communication unit 32 of the mobile information terminal 3 to the head-mounted display 4 in a wireless manner. The head-mounted display control information transmitted from the mobile information terminal 3 in a wireless manner is received by the head-mounted display-side wireless communication unit 52 of the head-mounted display 4 and is sent to the head-mounted display controller 55. The head-mounted display controller 55 performs switching from the ultrasound image non-display mode to the ultrasound image display mode in compliance with the head-mounted display control information.

In a case where the head-mounted display control information indicating the ultrasound image is to be displayed on the head-mounted display-side display unit 51 is received from the body controller 38, the head-mounted display data generation unit 36 of the mobile information terminal 3 executes various kinds of necessary processing, such as brightness correction, gradation correction, sharpness correction, image size correction, refresh rate correction, scanning frequency correction, and color correction compliant with the display format for the head-mounted display-side display unit 51, based on the ultrasound image signal sent from the terminal-side wireless communication unit 32 to the head-mounted display data generation unit 36 to generate an ultrasound image signal for the head-mounted display 4. The head-mounted display data generation unit 36 also executes various kinds of necessary processing, such as brightness correction, gradation correction, sharpness correction, image size correction, refresh rate correction, scanning frequency correction, and color correction compliant with the display format for the head-mounted display-side display unit 51, on the operation image generated by the operation image generation unit 37 to generate data corresponding to the operation image for the head-mounted display 4.

The head-mounted display data generation unit 36 generates head-mounted display data including the ultrasound image signal for the head-mounted display and the data corresponding to the operation image for the head-mounted display 4 generated in this manner, and sends the head-mounted display data to the terminal-side wireless communication unit 32 of the mobile information terminal 3. The head-mounted display data sent from the head-mounted display data generation unit 36 to the terminal-side wireless communication unit 32 is transmitted from the terminal-side wireless communication unit 32 to the head-mounted display 4 in a wireless manner.

The head-mounted display data transmitted from the mobile information terminal 3 in a wireless manner is received by the head-mounted display-side wireless communication unit 52 and is sent to the display controller 54. As shown in FIG. 6, the display controller 54 displays the head-mounted display ultrasound image UH and the head-mounted display operation image CS2 on the head-mounted display-side display unit 51 based on the head-mounted display data. In an example shown in FIG. 6, the head-mounted display ultrasound image UH and the head-mounted display operation image CS2 are displayed in the display region RD. The head-mounted display-side display unit 51 has transmittance, and thus, the user can view the subject P, the ultrasound probe 2, and the like through the head-mounted display-side display unit 51.

In a state in which the head-mounted display ultrasound image UH and the head-mounted display operation image CS2 are displayed on the head-mounted display-side display unit 51, the user performs an input operation through the touch sensor of the input unit 39 in compliance with the operation image CS1 displayed on the mobile information terminal-side display unit 34 to perform an operation regarding a display aspect of the head-mounted display-side display unit 51. For example, as shown in FIG. 3, in a case where the user touches the freeze button B6 displayed on the mobile information terminal-side display unit 34, head-mounted display control information indicating that the head-mounted display ultrasound image UH displayed on the head-mounted display-side display unit 51 is freeze-displayed is transmitted to the head-mounted display 4 through the terminal-side wireless communication unit 32 in a wireless manner, and the display of the head-mounted display ultrasound image UH displayed on the head-mounted display-side display unit 51 is frozen under the control of the head-mounted display controller 55.

In a case where the user touches the display-off button B8 displayed on the mobile information terminal-side display unit 34, head-mounted display control information indicating that the display of the head-mounted display ultrasound image UH displayed on the head-mounted display-side display unit 51 is to be turned off is transmitted to the head-mounted display 4 through the terminal-side wireless communication unit 32 in a wireless manner, and the ultrasound image non-display mode is selected by the head-mounted display controller 55. Though not shown, in a case where the ultrasound image non-display mode is selected by the head-mounted display controller 55, the head-mounted display-side display unit 51 is brought into a state in which the head-mounted display ultrasound image UH, the head-mounted display operation image CS2, and the display region RD are not displayed on the head-mounted display-side display unit 51. In this case, the user can view the field of view in front through the head-mounted display-side display unit 51 without being obstructed by the head-mounted display operation image CS2 and the display region RD.

In a case where the head-mounted display ultrasound image UH is not displayed on the head-mounted display-side display unit 51, the operation image CS1 and the terminal ultrasound image can be displayed on the mobile information terminal-side display unit 34. With this, even though the head-mounted display ultrasound image UH is not displayed on the head-mounted display-side display unit 51, the user can view the mobile information terminal-side display unit 34 to confirm the ultrasound image.

In this manner, the operation of the ultrasound system 1 of the invention is performed.

Incidentally, in a so-called stationary ultrasound diagnostic apparatus of the related art, usually, the ultrasound diagnostic apparatus is used by the user in a state in which the body of the ultrasound diagnostic apparatus is provided at a position away from the ultrasound probe, such as a bedside, and accordingly, there is difficulty in mobility, such as a limitation on a place where ultrasonography is performed. With the ultrasound system 1 of the invention, the user can perform ultrasonography on the subject by preparing the ultrasound probe 2, the mobile information terminal 3, and the head-mounted display 4 at hand, and can view the head-mounted display-side display unit 51 to confirm the head-mounted display ultrasound image UH. Therefore, it is possible to improve operability in a case where the user performs ultrasonography, and to improve mobility.

In the ultrasound system 1 according to Embodiment 1 of the invention, the user performs an input operation of the ultrasound system 1 by touching the operation image CS1 displayed on the mobile information terminal-side display unit 34, and the head-mounted display ultrasound image UH is displayed on the head-mounted display-side display unit 51 in compliance with the input operation of the user. Therefore, the user can easily perform the observation of the head-mounted display ultrasound image UH and the input operation for ultrasonography while examining the subject.

The head-mounted display operation image CS2 identical to the operation image CS1 displayed on the mobile information terminal-side display unit 34 is displayed on the head-mounted display-side display unit 51. Therefore, the user can recognize the disposition of the buttons in the operation image CS1 to perform an input operation through the input unit 39 of the mobile information terminal 3 without turning the eyes on the mobile information terminal 3 at hand.

The head-mounted display 4 selects any of the ultrasound image display mode and the ultrasound image non-display mode in compliance with the input operation of the user through the input unit 39 of the mobile information terminal 3. Therefore, the user can confirm the head-mounted display ultrasound image UH at a desired timing corresponding to an examination situation of the subject.

In Embodiment 1, although the head-mounted display operation image CS2 is displayed on the head-mounted display-side display unit 51, only the head-mounted display ultrasound image UH is displayed on the head-mounted display-side display unit 51, and the head-mounted display operation image CS2 may not be displayed. In this way, even though only the head-mounted display ultrasound image UH is displayed on the head-mounted display-side display unit 51, the user can easily perform the observation of the head-mounted display ultrasound image UH and the input operation for ultrasonography while examining the subject. Note that, as the head-mounted display operation image CS2 is displayed on the head-mounted display-side display unit 51, it is possible to further improve convenience in ultrasonography.

In Embodiment 1, although the B mode is used as the examination mode, the M mode or the like can also be used. Though not shown, as the image information data generation unit 19 may comprise a Doppler processing unit that executes so-called Doppler processing, the CD mode, the PD mode, the PW mode, the CW mode, and the like can also be used.

In such a case, it is desirable that, as buttons for setting the examination mode, buttons for inputting probe control information indicating that the M mode, the CD mode, the PD mode, the PW mode, the CW mode, and the like are to be used as the examination mode are included in the operation image CS1.

Though not shown, a measurement menu for selecting measurement items in performing measurement on the ultrasound image, a user interface, such as a keyboard for inputting information of the subject, a menu for selecting a body mark displayed on the ultrasound image in a superimposed manner, and the like can be displayed on the operation image CS1. Here, examples of the measurement items include measurement of a distance between two points on the ultrasound image, measurement of an area of a part on the ultrasound image, and measurement of a blood flow rate using a Doppler signal.

In a case where the measurement of the distance, the area, and the like is performed on the ultrasound image, for example, though not shown, a measurement unit that performs processing regarding the measurement can be provided in the mobile information terminal 3, and the user can touch a measurement caliper or the like on the terminal ultrasound image displayed on the mobile information terminal-side display unit 34 to perform the measurement of the distance, the area, and the like on the ultrasound image. In this case, the head-mounted display data generation unit 36 can generate, as the head-mounted display data, data that corresponds to the same display as the display on the mobile information terminal-side display unit 34 at present and complies with the display format for the head-mounted display 4, and can transmit the generated data to the head-mounted display 4 through the terminal-side wireless communication unit 32. With this, the user can perform the measurement on the ultrasound image while confirming the display on the head-mounted display-side display unit instead of confirming the display on the mobile information terminal-side display unit 34.

A body mark that is displayed on the ultrasound image in a superimposed manner can be displayed on the mobile information terminal-side display unit 34, a probe mark that is further displayed on the displayed body mark in a superimposed manner can be displayed, and the user may adjust the position of the displayed probe mark by a touch operation. Even in this case, the head-mounted display data generation unit 36 can generate, as the head-mounted display data, data that corresponds to the same display as the display on the mobile information terminal-side display unit 34 at present and complies with the display format for the head-mounted display 4, and can transmit the generated data to the head-mounted display 4 through the terminal-side wireless communication unit 32. Thereby, the user can adjust the position of the probe mark while confirming the display on the head-mounted display-side display unit 51 instead of confirming the display on the mobile information terminal-side display unit 34.

Small ultrasound images for use in operation confirmation of the ultrasound system 1 corresponding to the ultrasound image signals sequentially sent from the terminal-side wireless communication unit 32 can be displayed on the operation image CS1 displayed on the mobile information terminal-side display unit 34. In this case, the user can also confirm that, at present, the ultrasound probe 2 is in operation and the ultrasound image signals are sequentially acquired, by confirming the mobile information terminal-side display unit 34 instead of the head-mounted display-side display unit 51.

In a case where the user touches various buttons included in the operation image CS1 displayed on the mobile information terminal-side display unit 34, a display aspect of the button touched by the user can be changed. For example, the color of the button touched by the user can be changed or the color of the contour of the button touched by the user can be changed. With this, in the head-mounted display operation image CS2 displayed on the head-mounted display-side display unit 51, the display aspect of the same button as the button touched by the user in the operation image CS1 displayed on the mobile information terminal-side display unit 34 is changed. In this case, the user can more clearly recognize what kind of input operation the user performs at present by confirming the head-mounted display operation image CS2 displayed on the head-mounted display-side display unit 51.

An input operation can be performed in the ultrasound system 1 using a mechanical operation button that is provided in advance in the mobile information terminal 3.

In this case, a plurality of input systems are provided regarding the input operation of the user, whereby it is possible to further improve convenience in ultrasonography.

In Embodiment 1, although wireless communication is performed between the ultrasound probe 2 and the mobile information terminal 3 and between the mobile information terminal 3 and the head-mounted display 4, it is desirable that a wireless communication system between the ultrasound probe 2 and the mobile information terminal 3 is different from a wireless communication system between the mobile information terminal 3 and the head-mounted display 4 to keep each wireless communication state satisfactory.

For example, a frequency range in wireless communication between the ultrasound probe 2 and the mobile information terminal 3 can be different from a frequency range in wireless communication between the mobile information terminal 3 and the head-mounted display 4. For example, more specifically, a frequency in a range of 2.4 GHz can be used in wireless communication between the ultrasound probe 2 and the mobile information terminal 3, and a frequency in a range of 5 GHz can be used in wireless communication between the mobile information terminal 3 and the head-mounted display 4. For example, a communication standard for use in wireless communication between the ultrasound probe 2 and the mobile information terminal 3 can be different from a communication standard for use in wireless communication between the mobile information terminal 3 and the head-mounted display 4.

Figure 7:
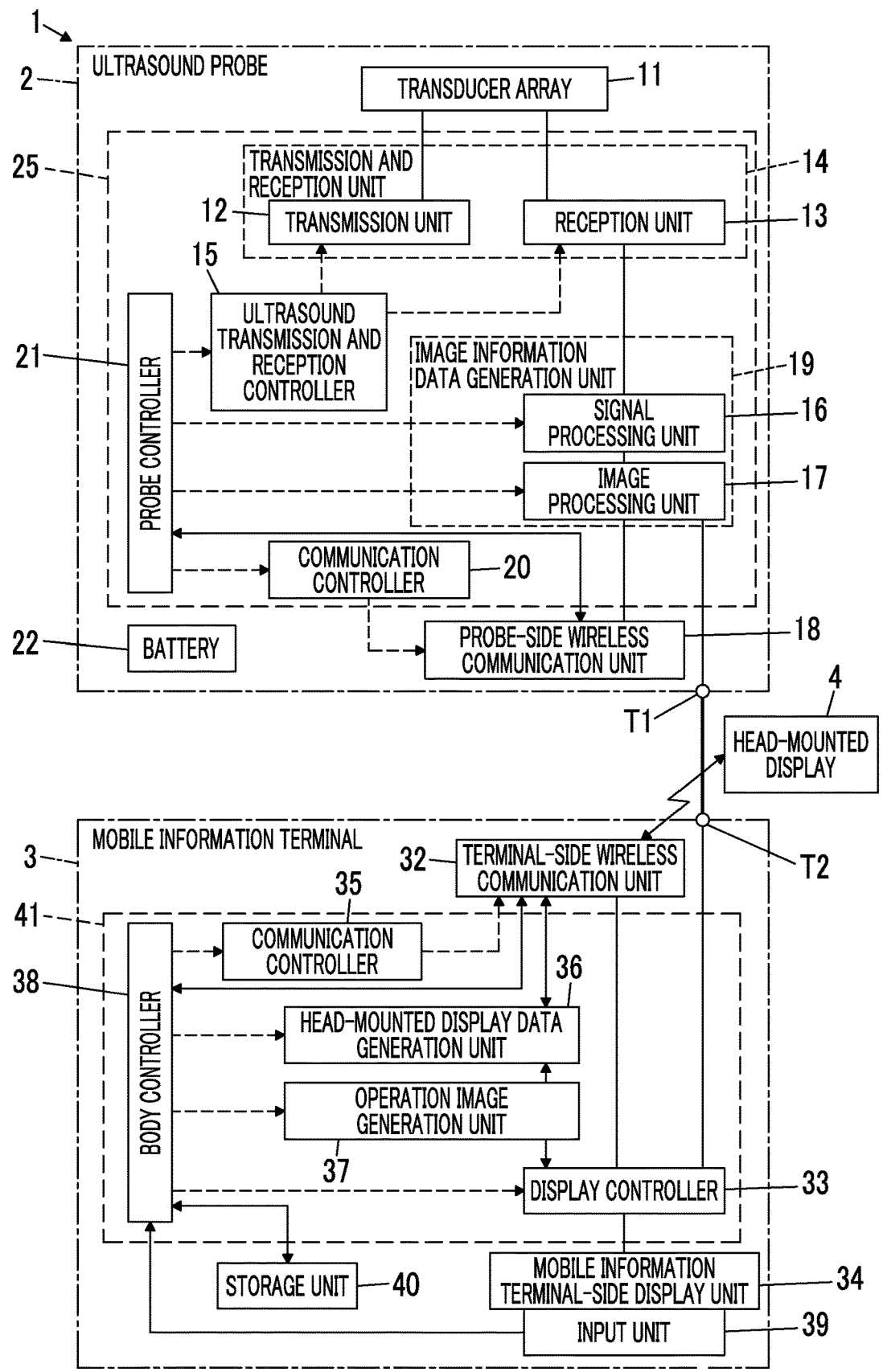
FIG. 7 is a block diagram showing the configuration of an ultrasound system according to a modification example of Embodiment 1 of the invention.

The ultrasound probe 2 and the mobile information terminal 3 can be connected in a wired manner instead of being connected in a wireless manner. Specifically, as shown in FIG. 7, the ultrasound probe 2 and the mobile information terminal 3 can be connected in a wired manner by connecting the probe-side connection terminal T1 of the ultrasound probe 2 and the terminal-side connection terminal T2 of the mobile information terminal 3 using a connection cable CC that can transmit information. In this case, the ultrasound system 1 can stop wireless connection between the ultrasound probe 2 and the mobile information terminal 3 by detecting the connection of the connection cable CC to the probe-side connection terminal T1 and the terminal-side connection terminal T2.

In this manner, it is possible to stabilize the communication state between the ultrasound probe 2 and the mobile information terminal 3.

In Embodiment 1, although the terminal ultrasound image is displayed on the mobile information terminal-side display unit 34, the head-mounted display ultrasound image UH can be constantly displayed on the head-mounted display-side display unit 51, instead of displaying only the operation image CS1 on the mobile information terminal-side display unit 34.

For example, in a case where the operation image CS1 and the terminal ultrasound image are displayed in the mobile information terminal 3, the operation image CS1 and the terminal ultrasound image can be displayed simultaneously or switchingly on the mobile information terminal-side display unit 34. With this, the user can perform ultrasonography on the subject while confirming the mobile information terminal-side display unit 34 even though the head-mounted display ultrasound image UH is not displayed on the head-mounted display-side display unit 51.

Though not shown, an external data memory that stores the ultrasound image signal and the like sent from the terminal-side wireless communication unit 32 can be connected to the mobile information terminal 3. As such an external data memory, a recording medium, such as a flash memory, a hard disc drive (HDD), an SSD, a flexible disc (FD), a magneto-optical disc (MO disc), a magnetic tape (MT), a RAM, a compact disc (CD), a digital versatile disc (DVD), an SD card, or a USB memory, or a server can be used. The mobile information terminal 3 and the external data memory can be connected in a wireless manner or can be connected in a wired manner.

Figure 8:
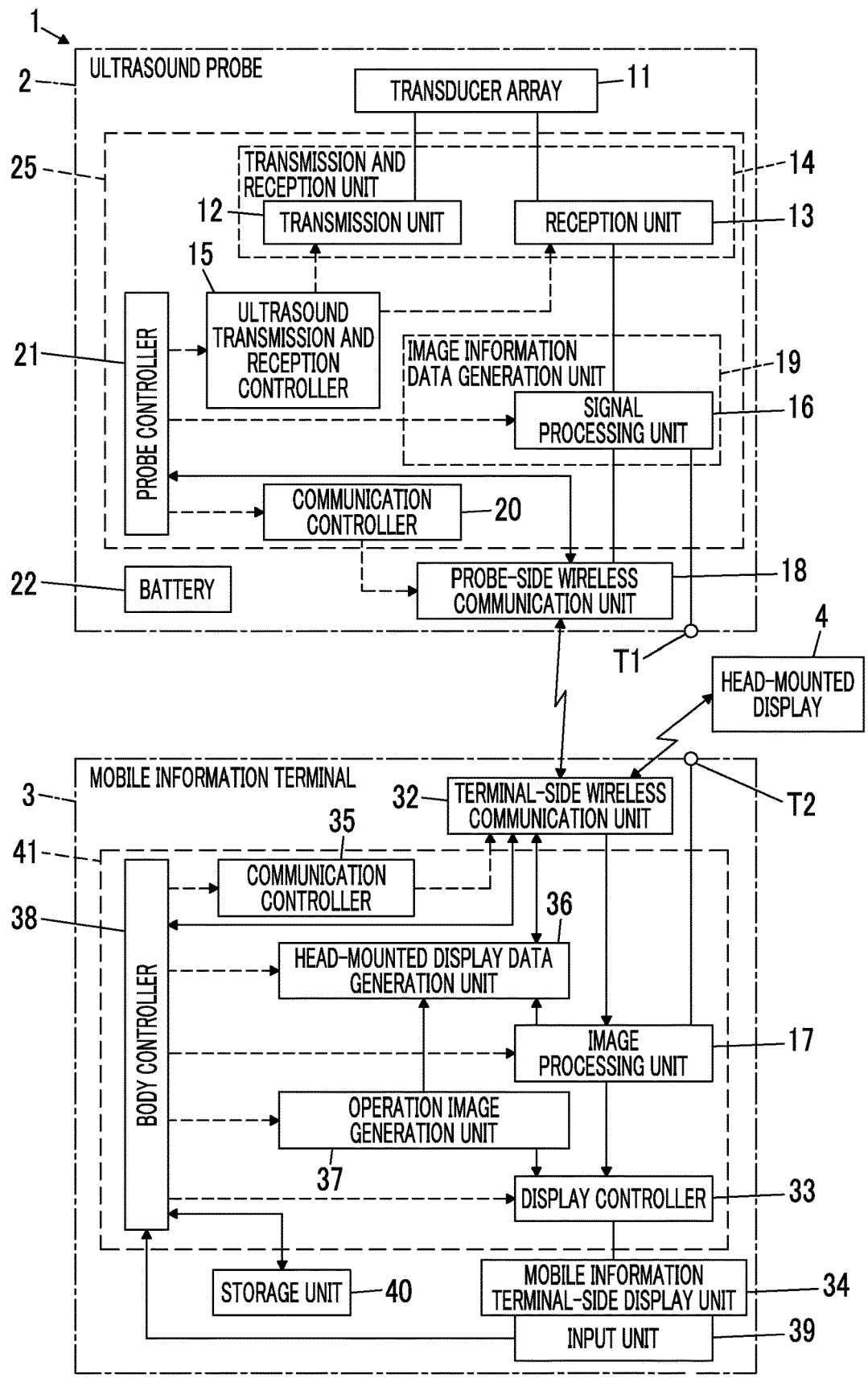
FIG. 8 is a block diagram showing the configuration of an ultrasound system according another modification example of Embodiment 1 of the invention.

In Embodiment 1, although the ultrasound image signal is generated in the ultrasound probe 2, and the generated ultrasound image signal is transmitted to the mobile information terminal 3 in a wireless manner, for example, a signal obtained by executing the envelope detection processing on the sound ray signal may be generated in the ultrasound probe 2, the generated signal may be transmitted to the mobile information terminal 3 in a wireless manner, and the ultrasound image signal may be generated based on the signal transmitted in a wireless manner in the mobile information terminal 3. Specifically, as shown in FIG. 8, the image information data generation unit 19 of the ultrasound probe 2 can comprise only the signal processing unit 16, and the mobile information terminal 3 can comprise the image processing unit 17. In this case, the probe-side wireless communication unit 18 and the probe-side connection terminal T1 are connected to the signal processing unit 16 of the image information data generation unit 19. The terminal-side wireless communication unit 32, the display controller 33, and the head-mounted display data generation unit 36 are connected to the image processing unit 17 of the mobile information terminal 3.

Here, the signal obtained by executing the envelope detection processing on the sound ray signal is generated as image information data by the image information data generation unit 19. The image information data generated by the image information data generation unit 19 is transmitted from the probe-side wireless communication unit 18 to the mobile information terminal 3, and the transmitted image information data is sent from the terminal-side wireless communication unit 32 to the image processing unit 17 of the mobile information terminal 3. The image processing unit 17 of the mobile information terminal 3 generates the ultrasound image signal based on the image information data received from the terminal-side wireless communication unit 32.

The generated ultrasound image signal is sent to the display controller 33 and the head-mounted display data generation unit 36. The ultrasound image signal received by the display controller 33 is displayed as the terminal ultrasound image on the mobile information terminal-side display unit 34 under the control of the display controller 33. The ultrasound image signal received by the head-mounted display data generation unit 36 is transmitted as the head-mounted display data from the terminal-side wireless communication unit 32 to the head-mounted display 4 in a wireless manner, and is displayed as the head-mounted display ultrasound image UH on the head-mounted display-side display unit 51.

In this way, even though the image information data generation unit 19 of the ultrasound probe 2 comprises only the signal processing unit 16, and the mobile information terminal 3 comprises the image processing unit 17, like a case where the image information data generation unit 19 of the ultrasound probe 2 comprises both the signal processing unit 16 and the image processing unit 17, the user can perform ultrasonography on the subject by preparing the ultrasound probe 2, the mobile information terminal 3, and the head-mounted display 4 at hand, and can view the head-mounted display-side display unit 51 to confirm the head-mounted display ultrasound image UH. Therefore, it is possible to improve operability in a case where the user performs ultrasonography, and to improve mobility.

Embodiment 2

In Embodiment 1, although the user performs the input operation through the input unit 39 of the mobile information terminal 3, the input operation can be performed based on voice of the user.

Figure 9:
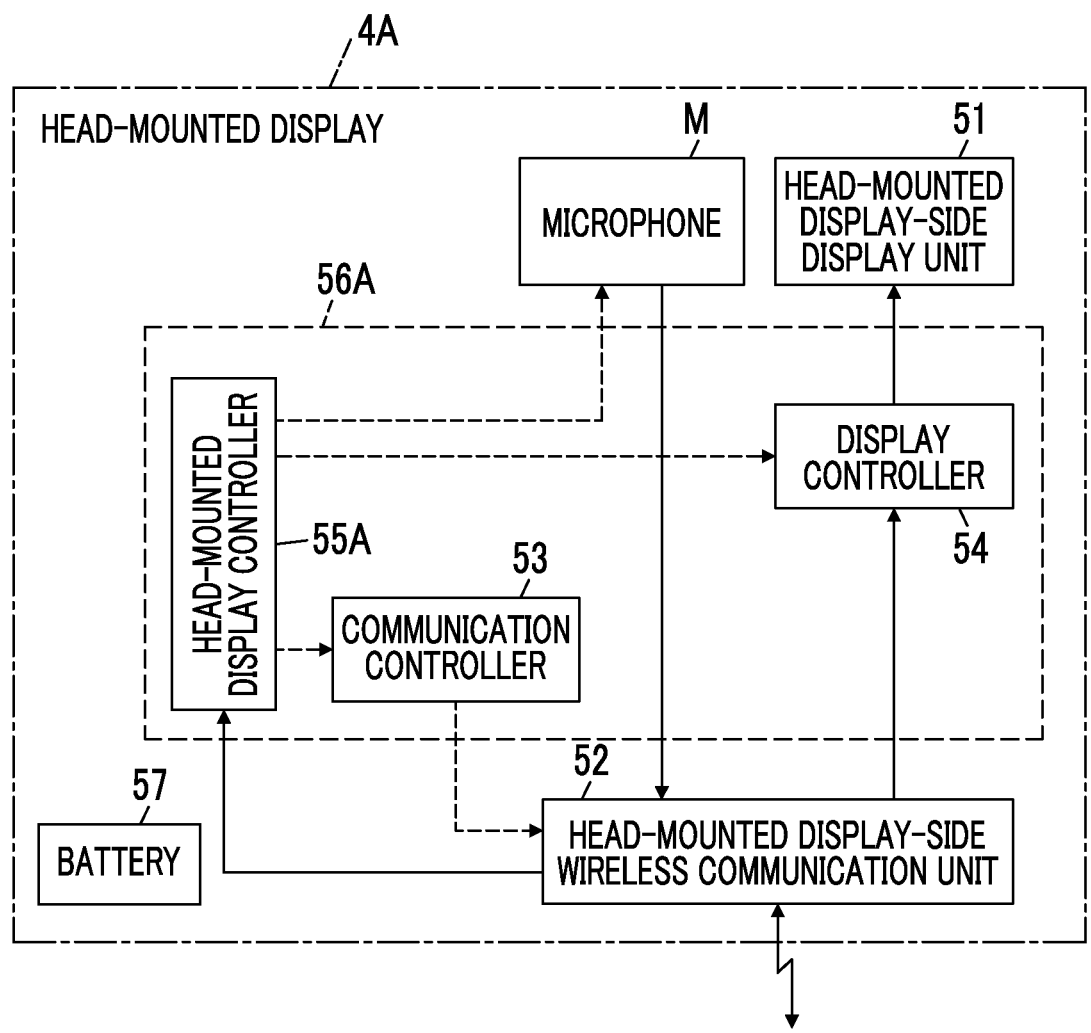
FIG. 9 is a block diagram showing the configuration of a head-mounted display in Embodiment 2 of the invention.

As shown in FIG. 9, a head-mounted display 4A of Embodiment 2 is additionally provided with a microphone M and comprises a head-mounted display controller 55A instead of the head-mounted display controller 55 compared to the head-mounted display 4 of Embodiment 1 shown in FIG. 5. In the head-mounted display 4A, the head-mounted display-side wireless communication unit 52 and the head-mounted display controller 55A are connected to the microphone M. The communication controller 53, the display controller 54, and the head-mounted display controller 55A constitute a head-mounted display processor 56A.

The microphone M of the head-mounted display 4A acquires the voice of the user. The microphone M acquires the voice of the user as an analog signal and converts the acquired voice into a digital signal to generate voice data. The voice data generated by the microphone M is sent to the head-mounted display-side wireless communication unit 52 and is transmitted from the head-mounted display-side wireless communication unit 52 to a mobile information terminal 3A shown in FIG. 10 in a wireless manner.

Figure 10:
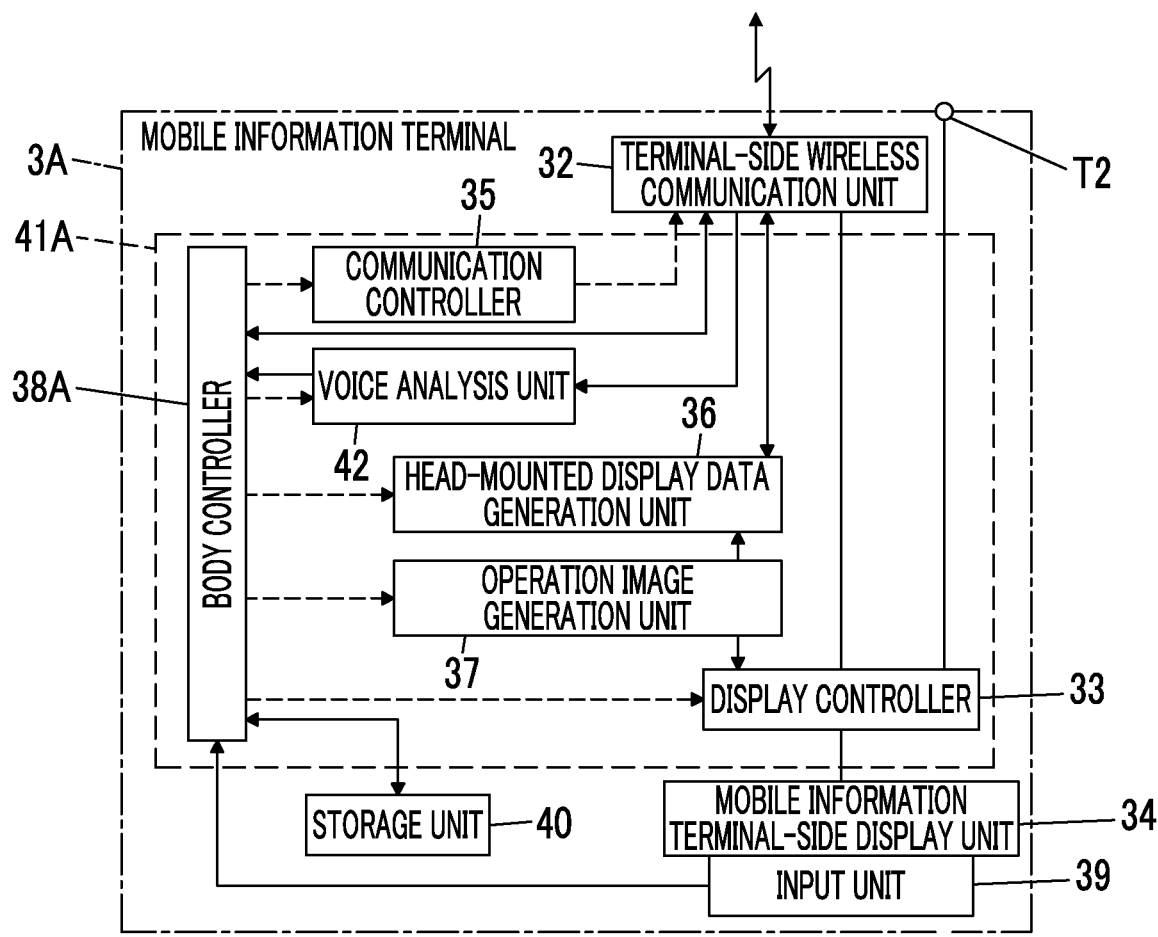
FIG. 10 is a block diagram showing the configuration of a mobile information terminal in Embodiment 2 of the invention.

As shown in FIG. 10, the mobile information terminal 3A of Embodiment 2 is additionally provided with a voice analysis unit 42 and comprises a body controller 38A instead of the body controller 38 compared to the mobile information terminal 3 of Embodiment 1 shown in FIG. 1. In the mobile information terminal 3A, the voice analysis unit 42 is connected to the terminal-side wireless communication unit 32, and the body controller 38A is connected to the voice analysis unit 42. The display controller 33, the communication controller 35, the head-mounted display data generation unit 36, the operation image generation unit 37, the body controller 38A, and the voice analysis unit 42 constitute a terminal processor 41A.

The voice analysis unit 42 of the terminal processor 41A receives the voice data generated by the microphone M of the head-mounted display 4A and transmitted from the head-mounted display-side wireless communication unit 52 in a wireless manner, through the terminal-side wireless communication unit 32 and analyzes the received voice data. The voice analysis unit 42 extracts the voice of the user based on the voice data, analyzes the extracted voice of the user, and sends the analyzed voice as input operation information representing an input operation from the user, to the body controller 38A. The body controller 38A performs control of each unit of the mobile information terminal 3A in compliance with the received input operation information.

For example, in a case where the user produces voice indicating that the ultrasound image is to be displayed on the head-mounted display-side display unit 51, the microphone M acquires the voice of the user, generates the voice data, and transmits the generated voice data from the head-mounted display-side wireless communication unit 52 to the mobile information terminal 3A in a wireless manner. The voice data transmitted in a wireless manner is sent to the voice analysis unit 42 of the mobile information terminal 3A through the terminal-side wireless communication unit 32 and is analyzed by the voice analysis unit 42. The voice analysis unit 42 analyzes the voice data and sends the input operation information indicating that the head-mounted display ultrasound image UH is to be displayed on the head-mounted display-side display unit 51, to the body controller 38A. The input operation information sent to the body controller 38A is sent as head-mounted display control information from the body controller 38 to the terminal-side wireless communication unit 32, is transmitted from the terminal-side wireless communication unit 32 to the head-mounted display 4A in a wireless manner, and is set to the head-mounted display controller 55A through the head-mounted display-side wireless communication unit 52. The head-mounted display controller 55A selects the ultrasound image display mode in compliance with the received head-mounted display control information. With this, the head-mounted display ultrasound image UH is displayed on the head-mounted display-side display unit 51.

In the same manner, in a case where the user produces voice indicating that the ultrasound image is to be not displayed on the head-mounted display-side display unit 51, the ultrasound image non-display mode is selected by the head-mounted display controller 55A, and the head-mounted display ultrasound image UH is not displayed on the head-mounted display-side display unit 51.

As described above, with the ultrasound system according to Embodiment 2, an input operation can be performed by the voice of the user. Therefore, for example, even though both hands of the user are used during ultrasonography, the user can easily perform the observation of the head-mounted display ultrasound image UH and the input operation for ultrasonography while examining the subject.

Embodiment 3

In Embodiment 2, although the input operation is performed based on the voice of the user, for example, the input operation can be performed based on movement of the eyes of the user, such as a wink or movement of a line of sight of the user.

Figure 11:
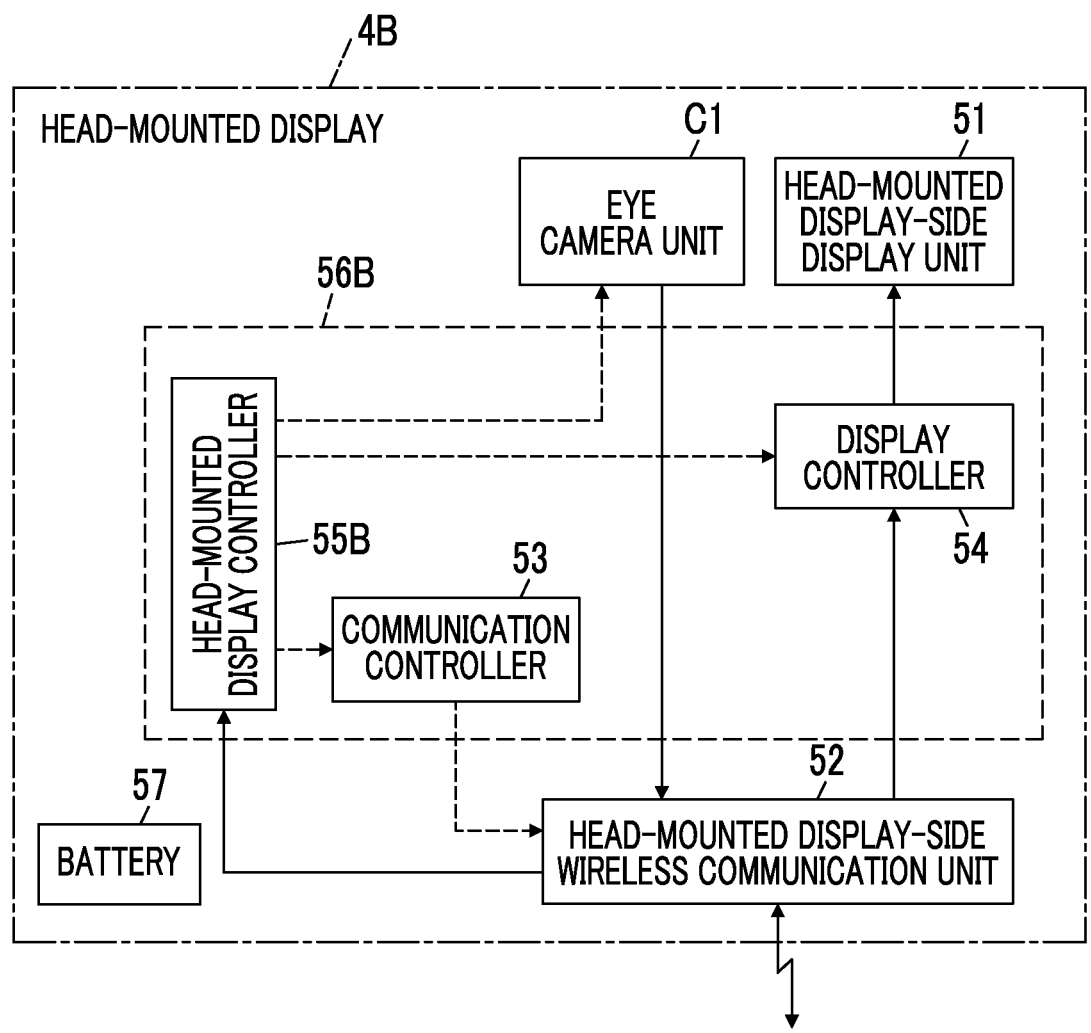
FIG. 11 is a block diagram showing the configuration of a head-mounted display in Embodiment 3 of the invention.

As shown in FIG. 11, a head-mounted display 4B of Embodiment 3 comprises an eye camera unit C1 instead of the microphone M and comprises a head-mounted display controller 55B instead of the head-mounted display controller 55A compared to the head-mounted display 4A of Embodiment 2 shown in FIG. 11.

In the head-mounted display 4B, the head-mounted display-side wireless communication unit 52 and the head-mounted display controller 55B are connected to the eye camera unit C1. The communication controller 53, the display controller 54, and the head-mounted display controller 55B constitute a head-mounted display processor 56B.

The eye camera unit C1 of the head-mounted display 4B continuously generates an eye image obtained by imaging the eyes of the user with a given frame rate. Though not shown, the eye camera unit C1 incorporates an imaging lens that faces the eyes of the user, an image sensor that images the eyes of the user through the imaging lens to acquire an eye image signal as an analog signal, an analog signal processing circuit that amplifies the eye image signal acquired by the image sensor to convert the eye image signal into a digital signal, and a digital signal processing circuit that performs various kinds of correction, such as gain correction, on the converted digital signal to generate an eye image. The analog signal processing circuit and the digital signal processing circuit can also be incorporated in the head-mounted display processor 56. The eye image generated by the eye camera unit 1C is transmitted from the head-mounted display-side wireless communication unit 52 to a mobile information terminal 3B shown in FIG. 12 in a wireless manner.

Figure 12:
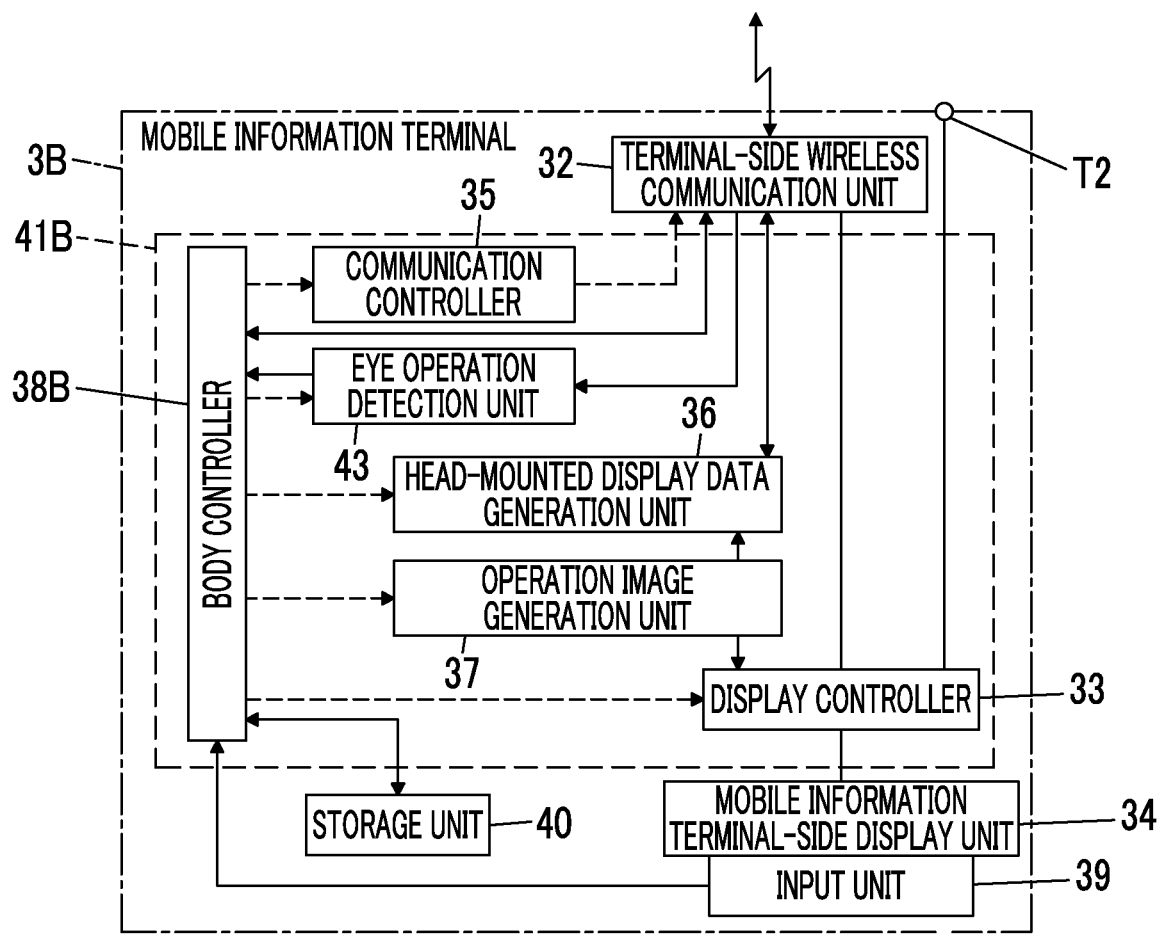
FIG. 12 is a block diagram showing the configuration of a mobile information terminal in Embodiment 3 of the invention.

As shown in FIG. 12, the mobile information terminal 3B of Embodiment 3 comprises an eye movement detection unit 43 instead of voice analysis unit 42 and a body controller 38B instead of the body controller 38A compared to the mobile information terminal 3A of Embodiment 2 shown in FIG. 2. In the mobile information terminal 3B, the eye movement detection unit 43 is connected to the terminal-side wireless communication unit 32, and the body controller 38B is connected to the eye movement detection unit 43. The display controller 33, the communication controller 35, the head-mounted display data generation unit 36, the operation image generation unit 37, the body controller 38B, and the eye movement detection unit 43 constitute a terminal processor 41B.

The eye movement detection unit 43 of the terminal processor 41B receives the eye image continuously generated by the eye camera unit C1 of the head-mounted display 4B and transmitted from the head-mounted display-side wireless communication unit 52 in a wireless manner, through the terminal-side wireless communication unit 32, and detects the movement of the eyes of the user, such as a wink or movement of the line of sight of the user, based on the received eye image. The eye movement detection unit 43 sends the detected movement of the eyes of the user as the input operation information representing the input operation from the user, to the body controller 38B. The body controller 38B performs control of each unit of the mobile information terminal 3B in compliance with the received input operation information.

Though not shown, for example, in a case where the head-mounted display ultrasound image UH is not displayed on the head-mounted display-side display unit 51, that is, in a case where the ultrasound image non-display mode is selected by the head-mounted display controller 55B, an item indicating that the ultrasound image is to be displayed on the head-mounted display-side display unit 51 can be displayed on the head-mounted display-side display unit 51, and the eye movement detection unit 43 can detect, as movement of the eyes of the user, a state in which the user keeps the eyes on the item for a given time. The eye movement detection unit 43 sends the detected movement of the eyes of the user to the body controller 38B. For example, the body controller 38B regards a state in which the user keeps the eyes on the item indicating that the ultrasound image is to be displayed, displayed on the head-mounted display-side display unit 51 as the input operation information indicating that the head-mounted display ultrasound image UH is to be displayed on the head-mounted display-side display unit 51 and sends the input operation information to the terminal-side wireless communication unit 32. The sent input operation information is transmitted as the head-mounted display control information from the terminal-side wireless communication unit 32 to the head-mounted display 4B in a wireless manner and is sent to the head-mounted display controller 55B through the head-mounted display-side wireless communication unit 52. The head-mounted display controller 55B selects the ultrasound image display mode in compliance with the received head-mounted display control information. With this, the head-mounted display ultrasound image UH is displayed on the head-mounted display-side display unit 51.

For example, in a case where the head-mounted display ultrasound image UH is displayed on the head-mounted display-side display unit 51, that is, in a case where the ultrasound image display mode is selected by the head-mounted display controller 55B, an item indicating that the ultrasound image is to be not displayed on the head-mounted display-side display unit 51 can be displayed on the head-mounted display-side display unit 51, and the eye movement detection unit 43 can detect, as the movement of the eyes of the user, a state in which the user keeps the eyes on the item for a given time. For example, the body controller 38B regards a state in which the user keeps the eyes on the item indicating that the ultrasound image is to be not displayed on the head-mounted display-side display unit 51, for a given time, as the input operation information indicating the head-mounted display ultrasound image UH is to be not displayed on the head-mounted display-side display unit 51 and sends the input operation information to the terminal-side wireless communication unit 32. The sent input operation information is transmitted as the head-mounted display control information from the terminal-side wireless communication unit 32 to the head-mounted display 4B in a wireless manner and is sent to the head-mounted display controller 55B through the head-mounted display-side wireless communication unit 52. With this, the ultrasound image non-display mode is selected by the head-mounted display controller 55B, and the head-mounted display ultrasound image UH is not displayed on the head-mounted display-side display unit 51.

As described above, with the ultrasound system according to Embodiment 3, the input operation can be performed by the movement of the eyes of the user. Therefore, for example, even though both hands of the user are used during ultrasonography, the user can easily perform the observation of the head-mounted display ultrasound image UH and the input operation for ultrasonography while examining the subject.

In Embodiment 1, the input operation is performed through the input unit 39 of the mobile information terminal 3, in Embodiment 2, the input operation is performed by the voice of the user, and in Embodiment 3, the input operation is performed by the movement of the eyes of the user; however, a method of the input operation is not limited thereto. Though not shown, for example, a so-called foot switch is may be provided in the ultrasound system and an input operation of the user may be performed through the foot switch. In this case, for example, in a case where the foot switch is pressed a given number of times within a certain time, an input operation to display the head-mounted display ultrasound image UH on the head-mounted display-side display unit 51 head-mounted display-side display unit 51, to not display the head-mounted display ultrasound image UH, or to freeze-display the head-mounted display ultrasound image UH on the head-mounted display-side display unit 51, or the like can be performed.

Embodiment 4

Detection regarding whether or not the head-mounted display-side display unit 51 is separated from a given disposition position, that is, whether or not the user views the field of view in front through the head-mounted display-side display unit 51, and the head-mounted display 4 can select any of the ultrasound image display mode and the ultrasound image non-display mode depending on a result of detection.

Figure 13:
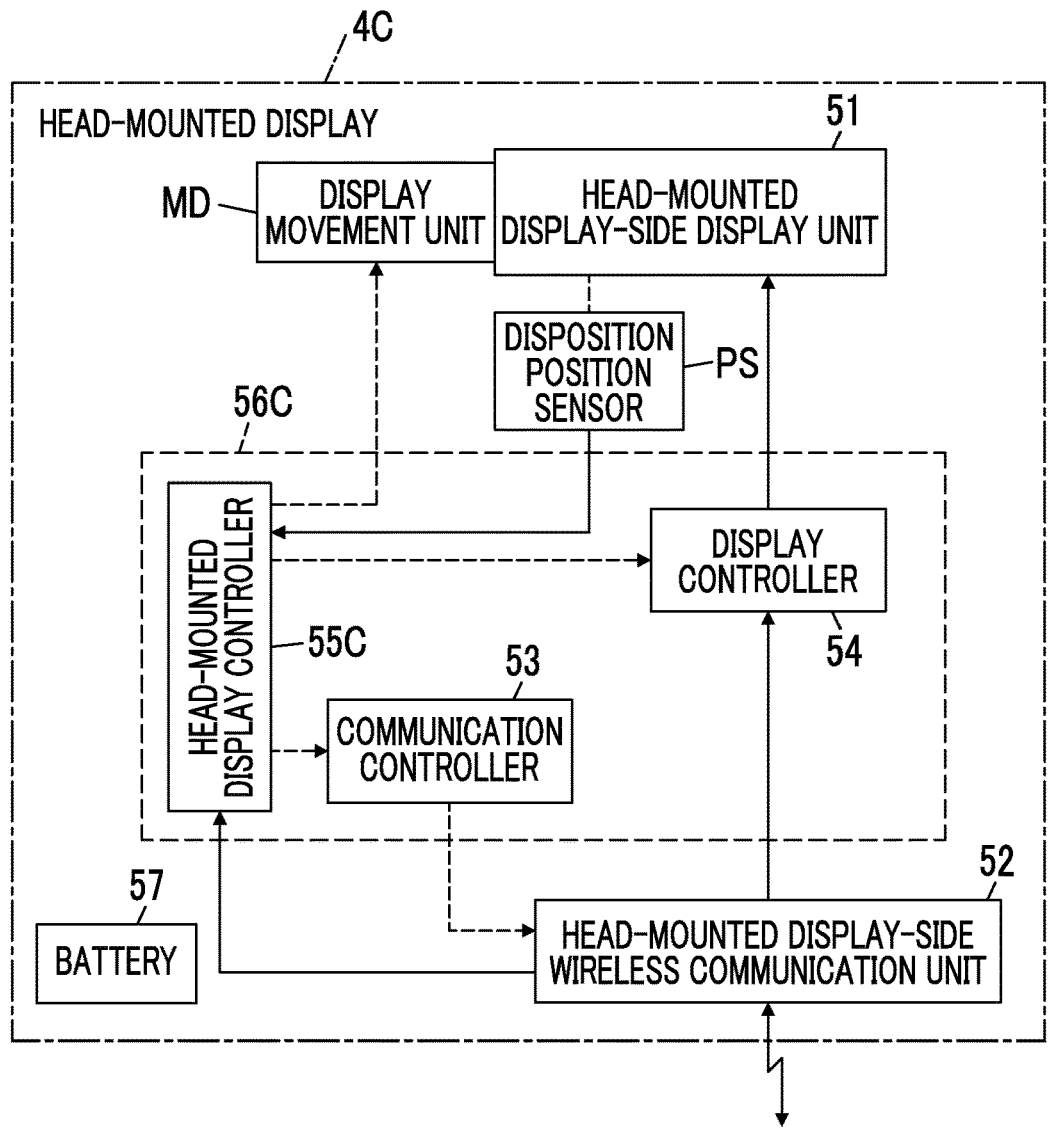
FIG. 13 is a block diagram showing the configuration of a head-mounted display in Embodiment 4 of the invention.

As shown in FIG. 13, a head-mounted display 4C of Embodiment 4 is additionally provided with a disposition position sensor PS and a display movement unit MD, and comprises a head-mounted display controller 55C instead of the head-mounted display controller 55 compared to the head-mounted display 4 of Embodiment 1 shown in FIG. 5. In the head-mounted display 4C, the disposition position sensor PS is disposed near the head-mounted display-side display unit 51, and the head-mounted display controller 55C is connected to the disposition position sensor PS. The display movement unit MD is connected to the head-mounted display-side display unit 51, and the head-mounted display controller 55C is connected to the display movement unit MD. The communication controller 53, the display controller 54, and the head-mounted display controller 55C constitute a head-mounted display processor 56C.

The disposition position sensor PS of the head-mounted display 4C is a sensor that detects whether or not the head-mounted display-side display unit 51 is positioned at the given disposition position. Here, the given disposition position of the head-mounted display-side display unit 51 is, for example, the position of the head-mounted display-side display unit 51 facing the eye EY of the user indicated by a dotted line in FIG. 14. In a case where the head-mounted display-side display unit 51 is positioned at the given disposition position, the user can clearly view the head-mounted display ultrasound image UH and the like displayed on the head-mounted display-side display unit 51 and can view the field of view in front through the head-mounted display-side display unit 51. A detection result of the disposition position sensor PS is sent to the head-mounted display controller 55C.

The head-mounted display controller 55C selects the ultrasound image display mode in a case where the disposition position sensor PS detects that the head-mounted display-side display unit 51 is positioned at the given disposition position, and selects the ultrasound image non-display mode in a case where the disposition position sensor PS detects that the head-mounted display-side display unit 51 is not positioned at the given disposition position.

With this, only in a case where the head-mounted display-side display unit 51 is positioned at the given disposition position, that is, only in a case where the user mounts the head-mounted display 4C and clearly views the head-mounted display-side display unit 51, the head-mounted display ultrasound image UH can be displayed on the head-mounted display-side display unit 51.

Figure 14:
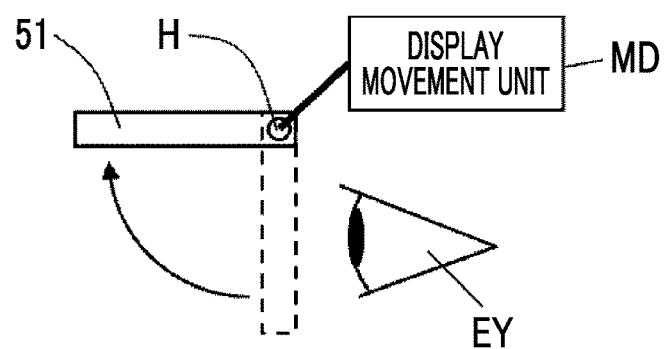
FIG. 14 is a diagram schematically showing a manner in which a head-mounted display-side display unit is moved in Embodiment 4 of the invention.

For example, as shown in FIG. 14, the head-mounted display-side display unit 51 is configured to rotate between the given disposition position and a given standby position different from the given disposition position around a pivot H. Here, the given standby position of the head-mounted display-side display unit 51 is the position of the head-mounted display-side display unit 51 indicated by a solid line in FIG. 14. In a case where the head-mounted display-side display unit 51 is positioned at the given standby position, the user can directly view the field of view in front without passing through the head-mounted display-side display unit 51.

The display movement unit MD of the head-mounted display 4C moves the head-mounted display-side display unit 51 between the given disposition position and the given standby position. Though not shown, the display movement unit MD incorporates, for example, an electric motor and moves the head-mounted display-side display unit 51 with drive power of the electric motor.

For example, in a case where the user performs an input operation indicating that the head-mounted display-side display unit 51 is to be moved to the given disposition position, through the input unit 39 of the mobile information terminal 3, as shown in FIG. 14, the display movement unit MD moves the head-mounted display-side display unit 51 to the disposition position under the control of the head-mounted display controller 55C. With this, the disposition position sensor PS detects that the head-mounted display-side display unit 51 is positioned at the given disposition position, the ultrasound image display mode is selected by the head-mounted display controller 55C in compliance with a detection result of the disposition position sensor PS, and the head-mounted display ultrasound image UH is displayed on the head-mounted display-side display unit 51.

For example, in a case where the user performs an input operation indicating that the head-mounted display-side display unit 51 is to be moved to the given standby position, through the input unit 39 of the mobile information terminal 3, the display movement unit MD moves the head-mounted display-side display unit 51 to the standby position under the control of the head-mounted display controller 55C. With this, the disposition position sensor PS detects that the head-mounted display-side display unit 51 is not positioned at the given disposition position, the ultrasound image non-display mode is selected by the head-mounted display controller 55C in compliance with a detection result of the disposition position sensor PS, and the head-mounted display ultrasound image UH is not displayed on the head-mounted display-side display unit 51. In this case, the terminal ultrasound image and the operation image CS1 are displayed on the mobile information terminal-side display unit 34.

As described above, with the ultrasound system according to Embodiment 4, the display movement unit MD of the head-mounted display 4C moves the head-mounted display-side display unit 51 between the given disposition position and the given standby position in compliance with the input operation of the user through the input unit 39 of the mobile information terminal 3, and the head-mounted display controller 55C selects any of the ultrasound image display mode and the ultrasound image non-display mode depending on the detection result of the disposition position sensor PS. Therefore, the user can confirm the head-mounted display ultrasound image UH at a desired timing corresponding to the examination situation of the subject.

In Embodiment 4, although the ultrasound image display mode is selected by the head-mounted display controller 55C in a case where the disposition position sensor PS detects that the head-mounted display-side display unit 51 is positioned at the given disposition position, in this state, the head-mounted display controller 55C can select any of the ultrasound image display mode and ultrasound image non-display mode further in compliance with the input operation of the user through the input unit 39 of the mobile information terminal 3.

In Embodiment 4, although the head-mounted display-side display unit 51 is automatically moved by the display movement unit MD, the user can manually move the head-mounted display-side display unit 51. Even in this case, the disposition position sensor PS detects whether or not the head-mounted display-side display unit 51 is positioned at the given disposition position, and the head-mounted display controller 55C selects any of the ultrasound image display mode and the ultrasound image non-display mode based on a detection result of the disposition position sensor PS.

Although application of the aspect of Embodiment 4 to Embodiment 1 has been described, the aspect of Embodiment 4 can be similarly applied to the aspects of Embodiment 2 and Embodiment 3. For example, in a case where the aspect of Embodiment 2 and the aspect of Embodiment 4 are combined, the display movement unit MD can move the head-mounted display-side display unit 51 between the given disposition position and the given standby position in compliance with an input operation by the voice of the user under the control of the head-mounted display controller 55C.

For example, in a case where the aspect of Embodiment 3 and the aspect of Embodiment 4 are combined, the display movement unit MD can move the head-mounted display-side display unit 51 between the given disposition position and the given standby position in compliance with an input operation by the movement of the eyes of the user under the control of the head-mounted display controller 55C.

Embodiment 5

In Embodiment 1, although the head-mounted display data is generated based on the image information data generated in the ultrasound probe 2, that is, the ultrasound image signal and the operation image generated in the mobile information terminal 3, a view image obtained by imaging the field of view in front of the user and head-mounted display data may be generated by adding the generated view image.

Figure 15:
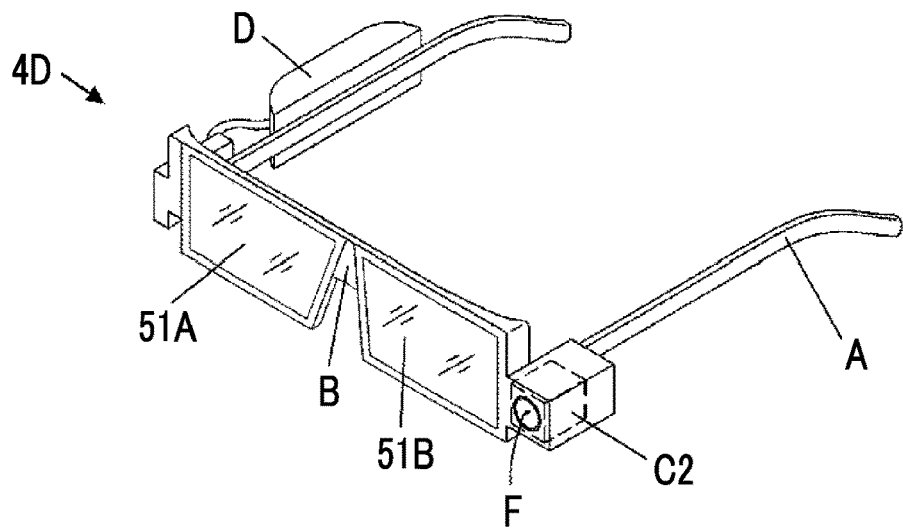
FIG. 15 is a diagram schematically showing a head-mounted display in Embodiment 5 of the invention.

As shown in FIG. 15, a head-mounted display 4D of Embodiment 5 comprises a view camera unit C2 that generates a view image obtained by imaging the field of view in front of the user. In an example shown in FIG. 15, the view camera unit C2 is attached to a connection portion of the left display unit 51B and the temple portion A, and an imaging lens F is disposed on the front surface of the view camera unit C2.

Figure 16:
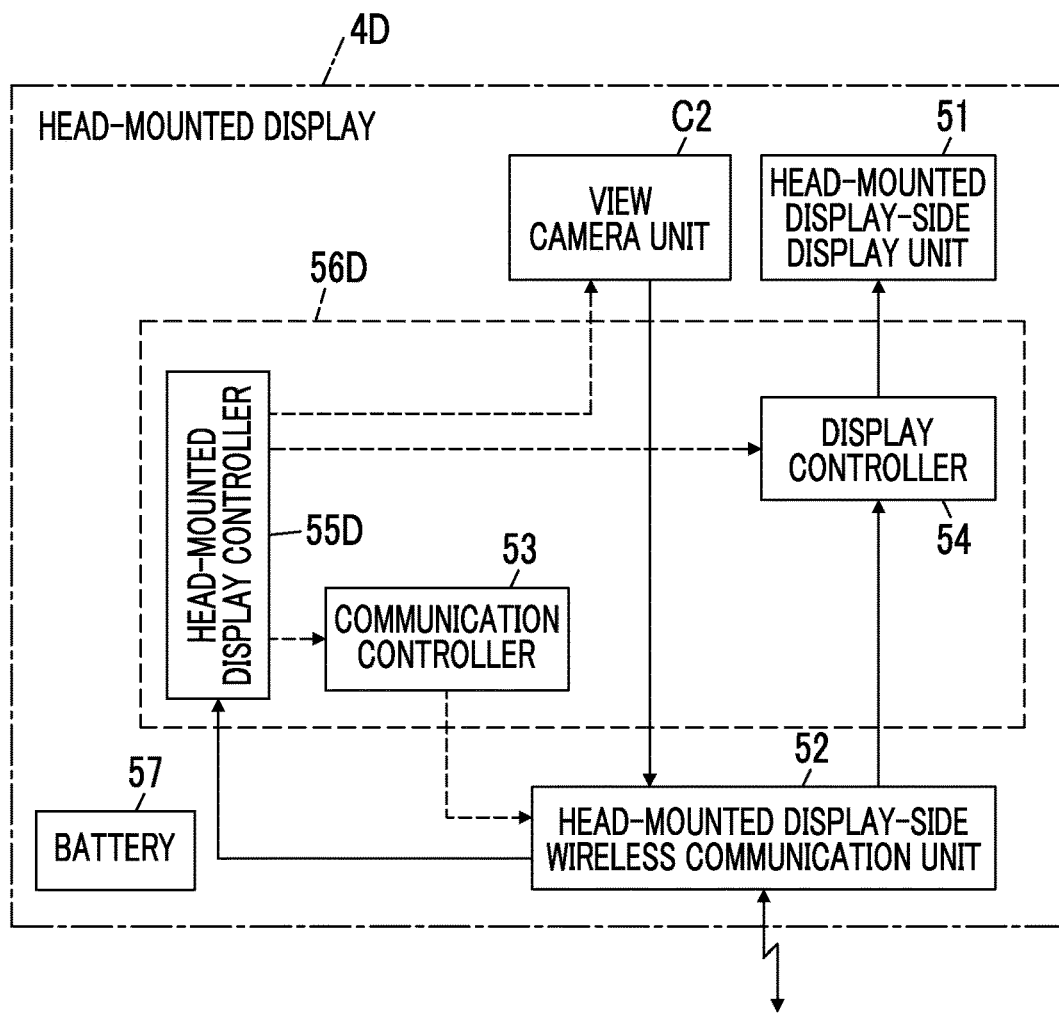
FIG. 16 is a diagram showing the configuration of the head-mounted display in Embodiment 5 of the invention.

As shown in FIG. 16, the head-mounted display 4D is additionally provided with the view camera unit C2 and comprises the head-mounted display controller 55D instead of the head-mounted display controller 55 compared to the head-mounted display 4 of Embodiment 1 shown in FIG. 5. The communication controller 53, the display controller 54, and the head-mounted display controller 55D constitute a head-mounted display processor 56D.

The view camera unit C2 of the head-mounted display 4D continuously generates the view image obtained by imaging the field of view in front of the user through the imaging lens F with a given frame rate. Though not shown, the view camera unit C2 incorporates an image sensor that images the field of view in front of the user through the imaging lens F to acquire a view image signal as an analog signal, an analog signal processing circuit that amplifies the view image signal acquired by the image sensor to convert the view image signal to a digital signal, and a digital signal processing circuit that performs various kinds of correction, such as gain correction, on the converted digital signal to generate a view image.

The analog signal processing circuit and the digital signal processing circuit can also be incorporated in the head-mounted display processor 56D.

Figure 17:
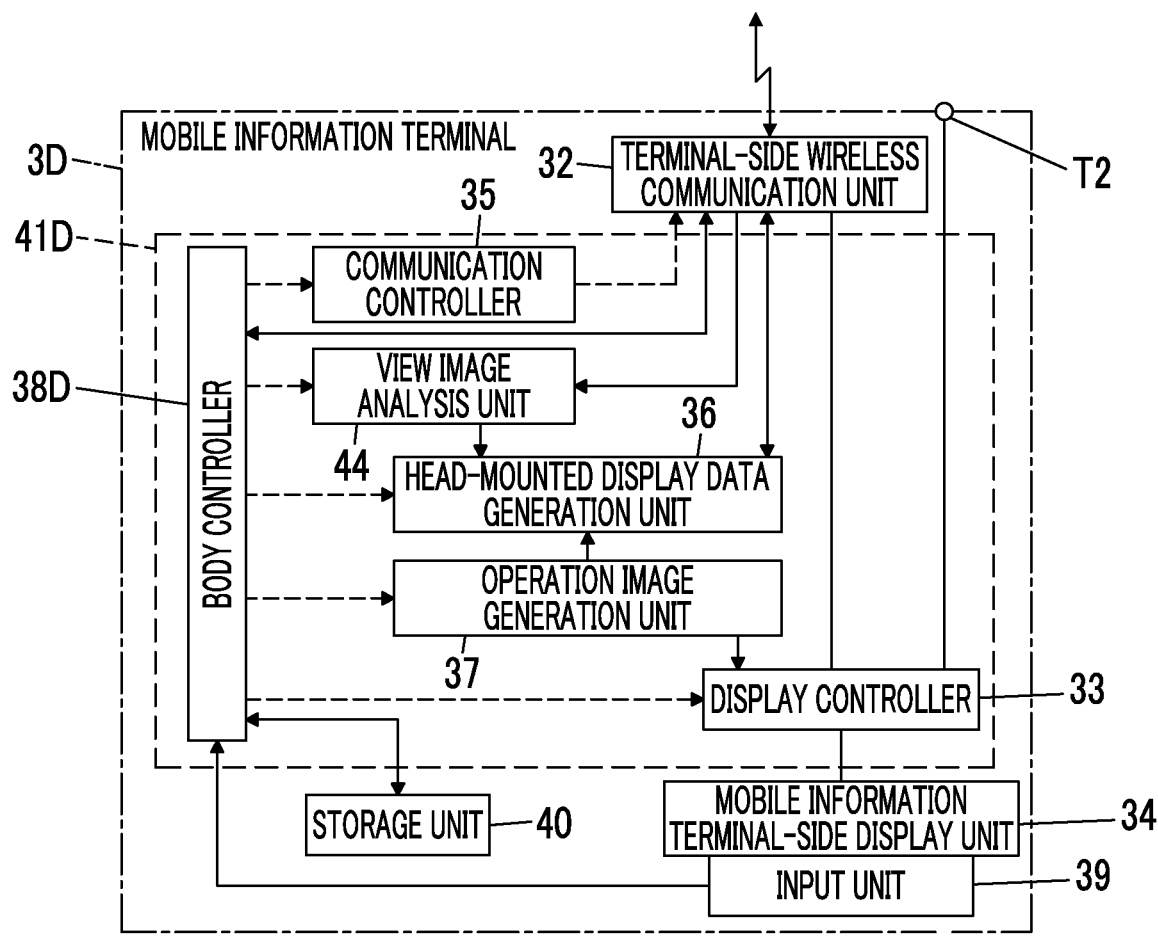
FIG. 17 is a block diagram showing the configuration of a mobile information terminal in Embodiment 5 of the invention.
Figure 18:
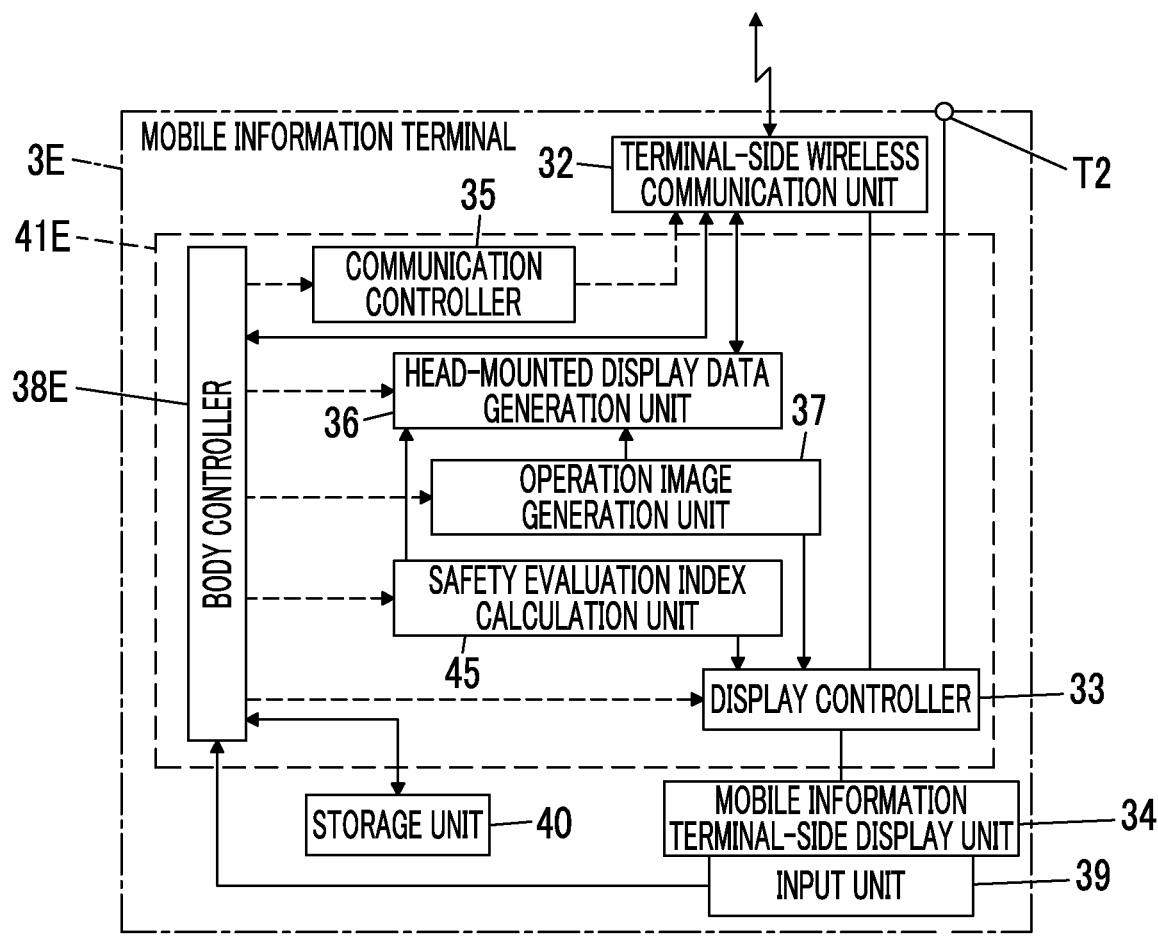
FIG. 18 is a block diagram showing the configuration of a mobile information terminal in Embodiment 6 of the invention.

The view image continuously generated by the view camera unit C2 is sent to the head-mounted display-side wireless communication unit 52 and is transmitted to a mobile information terminal 3D shown in FIG. 17 by the head-mounted display-side wireless communication unit 52 in a wireless manner.

As shown in FIG. 17, the mobile information terminal 3D of Embodiment 5 is additionally provided with a view image analysis unit 44 and comprises a body controller 38D instead of the body controller 38 compared to the mobile information terminal 3 of Embodiment 1 shown in FIG. 1. In the mobile information terminal 3D, the view image analysis unit 44 is connected to the terminal-side wireless communication unit 32, and the head-mounted display data generation unit 36 and the body controller 38D are connected to the view image analysis unit 44. The display controller 33, the communication controller 35, the head-mounted display data generation unit 36, the operation image generation unit 37, the body controller 38D, and the view image analysis unit 44 constitute a terminal processor 41D.

The view image analysis unit 44 of the terminal processor 41D receives the view image transmitted from the head-mounted display 4D in a wireless manner, through the terminal-side wireless communication unit 32 and performs image analysis on the received view image. For example, the view image analysis unit 44 detects a screen of the mobile information terminal-side display unit 34 shown in the received view image and sends a detection result to the head-mounted display data generation unit 36.

In a case where the view image analysis unit 44 detects the screen of the mobile information terminal-side display unit 34 shown in the view image, the head-mounted display data generation unit 36 of the terminal processor 41D generates head-mounted display data using a view image of a portion representing the screen of the mobile information terminal-side display unit 34 instead of the operation image generated by the operation image generation unit 37. The head-mounted display data generated in this manner is sent to the terminal-side wireless communication unit 32 and is transmitted to the head-mounted display 4D by the terminal-side wireless communication unit 32 in a wireless manner.

The head-mounted display data transmitted to the head-mounted display 4D in a wireless manner is sent to the display controller 54 through the head-mounted display-side wireless communication unit 52. With this, under the control of the display controller 54, the head-mounted display ultrasound image UH and the view image of the portion representing the screen of the mobile information terminal-side display unit 34 are displayed on the head-mounted display-side display unit 51 based on the head-mounted display data. In this case, for example, the view image of the portion representing the screen of the mobile information terminal-side display unit 34 is displayed instead of the head-mounted display operation image CS2 shown in FIG. 6.

With this, a finger of the user who touches the operation image CS1 displayed on the mobile information terminal-side display unit 34 is also displayed in the view image of the portion representing the screen of the mobile information terminal-side display unit 34. Therefore, the user can more reliably recognize the disposition of the buttons in the operation image CS1 to perform an input operation through the input unit 39 of the mobile information terminal 3 without turning the eyes on the mobile information terminal 3D.

For example, the view image analysis unit 44 can perform image analysis on the view image received from the terminal-side wireless communication unit 32 to calculate a distance between the view camera unit C2 of the head-mounted display 4D and the ultrasound probe 2 as a view distance of the user. For example, the view image analysis unit 44 can calculate the view distance of the user based on a difference in blurriness depending on the color using a so-called color aperture imaging model disclosed in "Imaging Technology Accomplishing Simultaneous Acquisition of Color Image and High-Precision Depth Map from Single Image Taken by Monocular Camera" (Toshiba Review VOL. 73, No. 1, January 2018).

In a case where the view image analysis unit 44 calculates the view distance of the user, the head-mounted display data generation unit 36 of the terminal processor 41D sets the sizes of the display region RD, the head-mounted display ultrasound image UH, the head-mounted display operation image CS2, and the view image of the portion representing the screen of the mobile information terminal-side display unit 34 that are displayed on the head-mounted display-side display unit 51, based on the calculated view distance of the user to generate head-mounted display data.

Here, for example, the head-mounted display data generation unit 36 can set the sizes of various images that are displayed on the head-mounted display-side display unit 51, by storing a relationship between the display region RD and the view distance of the user in advance and setting the sizes of the head-mounted display ultrasound image UH, the head-mounted display operation image CS2, and the view image of the portion representing the screen of the mobile information terminal-side display unit 34 to be a size in a certain proportion with respect to the size of the display region RD. For example, the head-mounted display data generation unit 36 can set the size of the display region RD to be greater as a value of the view distance of the user is smaller, and can set the size of the display region RD to be smaller as the view distance of the user is greater.

With this, the user can easily adjust the sizes of various images that are displayed head-mounted display-side display unit 51, by adjusting a standing position, a posture, and the like of the user.

As described above, with the ultrasound system according to Embodiment 5, the view image analysis unit 44 of the mobile information terminal 3D performs image analysis on the view image generated by the view camera unit C2 of the head-mounted display 4D, the head-mounted display data generation unit 36 generates the head-mounted display data by adding the result of the image analysis of the view image analysis unit 44, and various images, such as the head-mounted display ultrasound images UH, are displayed on the head-mounted display-side display unit 51 based on the generated head-mounted display data. Therefore, it is possible to improve convenience in ultrasonography.

Although application of the aspect of Embodiment 5 to Embodiment 1 has been described, the aspect of Embodiment 5 can be similarly applied to Embodiment 2 to Embodiment 4.

Embodiment 6

In the ultrasound system of Embodiment 1, although the ultrasound image and the like are displayed on the mobile information terminal-side display unit 34 and the head-mounted display-side display unit 51, it is preferable that a so-called safety evaluation index is displayed from a viewpoint of safety. Here, the safety evaluation index is an index for evaluating safety against the influence of ultrasonic waves on a living body, and includes, for example, a mechanical index (MI) value for evaluating safety of a mechanical action, such as radiation pressure and vibration of the ultrasonic waves in the living body, and a thermal index (TI) value for evaluating safety against a heating action of the living body caused by absorption of the energy of the ultrasonic waves in the living body.

A mobile information terminal 3E of Embodiment 6 is additionally provided with a safety evaluation index calculation unit 45 and comprises a body controller 38E instead of the body controller 38 compared to the mobile information terminal 3 of Embodiment 1 shown in FIG. 1. In the mobile information terminal 3E, the safety evaluation index calculation unit 45 is connected to the display controller 33 and the head-mounted display data generation unit 36, and the body controller 38E is connected to the safety evaluation index calculation unit 45. The display controller 33, the communication controller 35, the head-mounted display data generation unit 36, the operation image generation unit 37, the body controller 38E, and the safety evaluation index calculation unit 45 constitute a terminal processor 41E.

The safety evaluation index calculation unit 45 of the terminal processor 41E calculates the safety evaluation index based on conditions of transmission and reception of the ultrasonic waves controlled by the ultrasound transmission and reception controller 15 of the ultrasound probe 2 shown in FIG. 1 and sends the calculated safety evaluation index to the display controller 33 and the head-mounted display data generation unit 36. Here, the conditions of transmission and reception of the ultrasonic waves controlled by the ultrasound transmission and reception controller 15 of the probe processor 25 include a scanning rate in the transmission and reception unit 14 of the probe processor 25, the intensity of the ultrasonic waves transmitted from the transducer array 11 into the subject, that is, the level of a voltage of the drive signal transmitted from the transmission unit 12, a center frequency of the ultrasonic waves, and an amplification factor of the reception signal.

In a case where the MI value is calculated as the safety evaluation index by the safety evaluation index calculation unit 45, for example, the MI value is calculated by dividing the maximum negative sound pressure of the ultrasonic waves considering attenuation in the living body by the square root of the center frequency of the ultrasonic waves transmitted from the transducer array 11. In a case where the TI value is calculated as the safety evaluation index by the safety evaluation index calculation unit 45, for example, the TI value is calculated by dividing a the output intensity of the ultrasonic waves in the living body by the output intensity of the ultrasonic waves necessary for increasing a temperature of a tissue of the living body by 1° C.

The safety evaluation index, such as the MI value or the TI value calculated by the safety evaluation index calculation unit 45 in this manner is displayed on the mobile information terminal-side display unit 34 under the control of the display controller 33. The safety evaluation index calculated by the safety evaluation index calculation unit 45 is subjected to various kinds of processing in the head-mounted display data generation unit 36 under the control of the body controller 38E and is transmitted as head-mounted display data compliant with the display format for the head-mounted display 4 to the head-mounted display 4 through the terminal-side wireless communication unit 32 in a wireless manner. The safety evaluation index transmitted to the head-mounted display 4 in a wireless manner in this manner is displayed on the head-mounted display-side display unit 51.

Here, it is desirable that the safety evaluation index is constantly displayed on the mobile information terminal-side display unit 34 while ultrasonography using the ultrasound probe 2 is performed. In this case, the safety evaluation index can be displayed on the mobile information terminal-side display unit 34 along with the terminal ultrasound image or the operation image CS1. With this, for example, even though a wireless communication state between the mobile information terminal 3E and the head-mounted display 4 is degraded, the user can recognize the influence of the ultrasonic waves transmitted from the transducer array 11 on the inside of the subject by confirming at least the value of the safety evaluation index displayed on the mobile information terminal-side display unit 34.

As described above, with the ultrasound system according to Embodiment 6, the safety evaluation index calculation unit 45 of the terminal processor 41E calculates the safety evaluation index, such as the MI value or the TI value, and the calculated safety evaluation index is displayed on the mobile information terminal-side display unit 34 and the head-mounted display-side display unit 51. Therefore, the user can recognize the influence of the ultrasonic waves transmitted from the transducer array 11 on the inside of the subject by confirming the safety evaluation index displayed on the mobile information terminal-side display unit 34 and the head-mounted display-side display unit 51. The safety evaluation index calculated by the safety evaluation index calculation unit 45 is constantly displayed on the mobile information terminal-side display unit 34. Therefore, even though the wireless communication state between the mobile information terminal 3E and the head-mounted display 4 is degraded, the user can confirm the safety evaluation index.

Although application of the aspect of Embodiment 6 to Embodiment 1 has been described, the aspect of Embodiment 6 can be similarly applied to Embodiment 2 to Embodiment 5.

Embodiment 7

In Embodiment 1, although the ultrasound probe 2 and the head-mounted display 4 are connected to the mobile information terminal 3 in a wireless state, and the head-mounted display data, the operation image CS1, and the like are generated in the mobile information terminal 3, the ultrasound probe 2, the mobile information terminal 3, and the head-mounted display 4 can be connected to an external server through a network, and the external server, instead of the mobile information terminal 3, can generate the head-mounted display data, the operation image CS1, and the like.

Figure 19:
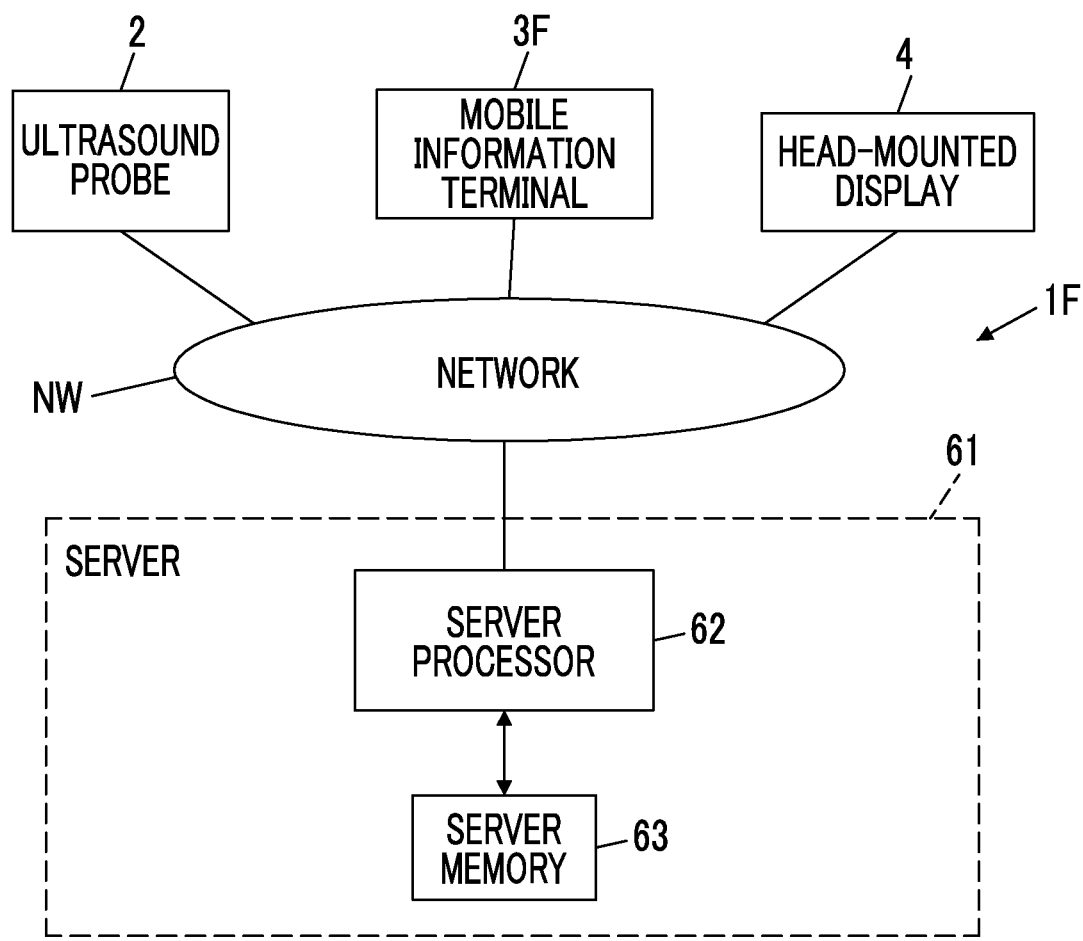
FIG. 19 is a block diagram showing the configuration of an ultrasound system according to Embodiment 7 of the invention.

As shown in FIG. 19, an ultrasound system 1F according to Embodiment 7 has a configuration in which the ultrasound probe 2, a mobile information terminal 3F, and the head-mounted display 4 are connected to a server 61 through a network NW. Though not shown, the mobile information terminal 3F has a configuration in which the head-mounted display data generation unit 36 and the operation image generation unit 37 are excluded compared to the mobile information terminal 3 of Embodiment 1 shown in FIG. 1.

The server 61 has a server processor 62 that is connected to the network NW, and a server memory 63 is connected to the server processor 62.

The server memory 63 stores an operation program of the server 61, and the like. As the server memory 63, a flash memory, an SSD, an HDD, or the like can be used.

Though not shown, the server processor 62 is a processor including the head-mounted display data generation unit 36 and the operation image generation unit 37 in the mobile information terminal 3 of Embodiment 1 shown in FIG. 1. The server processor 62 generates the operation image CS1 and transmits the generated operation image CS1 to the mobile information terminal 3F through the network NW. The server processor 62 generates the head-mounted display data using the generated operation image CS1 and the ultrasound image signal received from the ultrasound probe 2 through the network NW and transmits the generated head-mounted display data to the head-mounted display 4 through the network NW.

The mobile information terminal 3F displays the terminal ultrasound image on the mobile information terminal-side display unit 34 based on the ultrasound image signal transmitted from the ultrasound probe 2 by way of the server 61 and displays the operation image CS1 transmitted from the server processor 62 through the network NW on the mobile information terminal-side display unit 34. In a case where the user touches the operation image CS1 displayed on the mobile information terminal-side display unit 34, various kinds of input operation information are transmitted to the ultrasound probe 2, the head-mounted display 4, and the server 61 by way of the network NW, and the ultrasound probe 2, the head-mounted display 4, and the server 61 are controlled.

The head-mounted display 4 displays the head-mounted display ultrasound image UH, the head-mounted display operation image CS2, and the like on the head-mounted display-side display unit 51 based on the head-mounted display data transmitted from the server processor 62 through the network NW.

As described above, with the ultrasound system 1F according to Embodiment 7, like the ultrasound system 1 of Embodiment 1, the user can perform ultrasonography on the subject by preparing the ultrasound probe 2, the mobile information terminal 3, and the head-mounted display 4 at hand, and can view the head-mounted display-side display unit 51 to confirm the head-mounted display ultrasound image UH. Therefore, it is possible to improve operability in a case where the user performs ultrasonography, and to improve mobility.

Although application of the aspect of Embodiment 7 to Embodiment 1 has been described, the aspect of Embodiment 7 can be similarly applied to Embodiment 2 to Embodiment 6.

EXPLANATION OF REFERENCES 1, 1F: ultrasound system
2: ultrasound probe
3, 3A, 3B, 3D, 3E, 3F: mobile information terminal
4, 4A, 4B, 4C, 4D: head-mounted display
11: transducer array
12: transmission unit
13: reception unit
14: transmission and reception unit
15: ultrasound transmission and reception controller
16: signal processing unit
17: image processing unit
18: probe-side wireless communication unit
19: image information data generation unit
20, 35, 53: communication controller
21: probe controller
22, 57: battery
25: probe processor
26: amplification unit
27: AD conversion unit
28: beamformer
32: terminal-side wireless communication unit
33, 54: display controller
34: mobile information terminal-side display unit
36: head-mounted display data generation unit
37: operation image generation unit
38, 38A, 38B, 38D, 38E: body controller
39: input unit
40: storage unit
41, 41A, 41B, 41D, 41E: terminal processor
42: voice analysis unit
43: eye movement detection unit
44: view image analysis unit
45: safety evaluation index calculation unit
51: head-mounted display-side display unit
51A, 51B: display unit
52: head-mounted display-side wireless communication unit
55, 55A, 55B, 55C, 55D: head-mounted display controller
56, 56A, 56B, 56C, 56D: head-mounted display processor
61: server
62: server processor
63: server memory
A: temple portion
B: bridge portion
C1: eye camera unit
C2: view camera unit
CS1: operation image
CS2: head-mounted display operation image
D: accommodation portion
EY: eye of user
F: imaging lens
H: hinge
M: microphone
MD: display movement unit
NW: network
P: subject
PS: disposition position sensor
RD: display region
T1: probe-side connection terminal
T2: terminal-side connection terminal
UH: head-mounted display ultrasound image.

What is claimed is:

1. An ultrasound system in which a mobile information terminal is connected to an ultrasound probe and a head-mounted display having a head-mounted display-side display unit,
wherein the ultrasound probe includes
a transducer array,
a first processor configured to transmit an ultrasonic wave from the transducer array and generate a sound ray signal based on a reception signal acquired by the transducer array, and generate image information data based on the sound ray signal, and
a probe-side wireless communication unit configured to transmit the image information data to the mobile information terminal in a wireless manner by using a first wireless communication system,
the mobile information terminal includes
a mobile information terminal-side display unit,
an input unit that includes a touch sensor disposed to be superimposed on the mobile information terminal-side display unit and is used by a user to perform an input operation,
a second processor configured to generate an operation image that is displayed on the mobile information terminal-side display unit and is used by the user to perform the input operation through the touch sensor, and configured to generate head-mounted display data having a display format for the head-mounted display-side display unit based on the image information data transmitted from the ultrasound probe in the wireless manner, and
a terminal-side wireless communication unit configured to transmit the head-mounted display data generated by the second processor to the head-mounted display in the wireless manner by using a second wireless communication system which is different from the first wireless communication system, and
the head-mounted display is configured to display a head-mounted display ultrasound image on the head-mounted display-side display unit based on the head-mounted display data transmitted from the mobile information terminal in the wireless manner.

2. The ultrasound system according to claim 1, wherein the head-mounted display data includes data corresponding to the head-mounted display ultrasound image and the operation image generated by the second processor, and the head-mounted display is configured to display the head-mounted display ultrasound image and a head-mounted display operation image identical to the operation image displayed on the mobile information terminal-side display unit on the head-mounted display-side display unit based on the head-mounted display data.

3. The ultrasound system according to claim 1, wherein the head-mounted display further includes a view camera unit configured to generate a view image obtained by imaging a field of view in front of the user, the second processor is configured to perform image analysis on the view image generated by the view camera unit, and generate the head-mounted display data by adding a result of the image analysis of the view image.

4. The ultrasound system according to claim 3, wherein the second processor is configured to detect a screen of the mobile information terminal-side display unit shown in the view image generated by the view camera unit, the head-mounted display data includes data corresponding to the head-mounted display ultrasound image and the screen of the mobile information terminal-side display unit detected by the second processor, and the head-mounted display is configured to display the head-mounted display ultrasound image and a terminal screen image representing the screen of the mobile information terminal-side display unit detected by the second processor on the head-mounted display-side display unit based on the head-mounted display data.

5. The ultrasound system according to claim 3, wherein the second processor is configured to calculate a distance between the ultrasound probe and the view camera unit based on the view image generated by the view camera unit, and set a size of a display region where the head-mounted display ultrasound image is displayed in the head-mounted display-side display unit, based on the distance calculated to generate the head-mounted display data, and the head-mounted display is configured to display the head-mounted display ultrasound image on the head-mounted display-side display unit based on the head-mounted display data with the size of the display region set by the second processor.

6. The ultrasound system according to claim 1, wherein a frequency range in wireless communication between the mobile information terminal and the ultrasound probe is different from a frequency range in wireless communication between the mobile information terminal and the head-mounted display.

7. The ultrasound system according to claim 1, wherein the second processor is configured to calculate a safety evaluation index based on conditions of transmission and reception of the ultrasonic wave in the ultrasound probe and display the safety evaluation index on the mobile information terminal-side display unit.

8. The ultrasound system according to claim 1, wherein the image information data is a signal obtained by executing attenuation correction and envelope detection processing depending on a depth of a reflection position of the ultrasonic wave on the sound ray signal generated by the first processor.

9. The ultrasound system according to claim 1, wherein the image information data is an ultrasound image signal obtained by executing attenuation correction and envelope detection processing depending on a reflection position of the ultrasonic wave on the sound ray signal generated by the first processor and converting the sound ray signal in compliance with a given image display system.

10. The ultrasound system according to claim 1, wherein the first processor is configured to direct the transducer array to transmit the ultrasonic wave, and generate the sound ray signal based on the reception signal acquired by the transducer array.

11. The ultrasound system according to claim 1, wherein the head-mounted display is configured to have an ultrasound image display mode in which the head-mounted display ultrasound image is displayed on the head-mounted display-side display unit and an ultrasound image non-display mode in which the head-mounted display ultrasound image is not displayed on the head-mounted display-side display unit.

12. The ultrasound system according to claim 11, wherein the head-mounted display is configured to select any of the ultrasound image display mode and the ultrasound image non-display mode in compliance with an input operation of the user on the operation image through the touch sensor of the mobile information terminal.

13. The ultrasound system according to claim 11, wherein the head-mounted display further includes a microphone, the second processor is configured to analyze voice of the user acquired by the microphone of the head-mounted display, and the head-mounted display is configured to select any of the ultrasound image display mode and the ultrasound image non-display mode in compliance with the voice of the user acquired by the microphone and analyzed by the second processor.

14. The ultrasound system according to claim 11, wherein the head-mounted display further includes an eye camera unit configured to generate an eye image obtained by imaging eyes of the user, the second processor is configured to detect movement of the eyes of the user based on the eye image generated by the eye camera unit, and the head-mounted display is configured to select any of the ultrasound image display mode and the ultrasound image non-display mode in compliance with the movement of the eyes of the user detected by the second processor.

15. The ultrasound system according to claim 11, wherein the head-mounted display further includes a disposition position sensor configured to detect whether or not the head-mounted display-side display unit is positioned at a given disposition position with respect to a head of the user, and the head-mounted display is configured to select the ultrasound image display mode in a case where the disposition position sensor detects that the head-mounted display-side display unit is positioned at the given disposition position, and select the ultrasound image non-display mode in a case where the disposition position sensor detects that the head-mounted display-side display unit is not positioned at the given disposition position.

16. The ultrasound system according to claim 15,
wherein the head-mounted display further includes a display movement unit configured to move the head-mounted display-side display unit between the given disposition position and a given standby position different from the given disposition position.

17. The ultrasound system according to claim 16,
wherein the head-mounted display further includes a microphone,
the second processor is configured to analyze voice of the user acquired by the microphone of the head-mounted display, and
the display movement unit of the head-mounted display is configured to move the head-mounted display-side display unit in compliance with the voice of the user acquired by the microphone and analyzed by the second processor.

18. The ultrasound system according to claim 16,
wherein the head-mounted display further includes an eye camera unit configured to generate an eye image obtained by imaging eyes of the user,
the second processor is configured to detect movement of the eyes of the user based on the eye image generated by the eye camera unit, and
the display movement unit of the head-mounted display is configured to move the head-mounted display-side display unit in compliance with the movement of the eyes of the user detected by the second processor.

19. The ultrasound system according to claim 11,
wherein the mobile information terminal is configured to display the operation image and a terminal ultrasound image based on the image information data generated by the first processor on the mobile information terminal-side display unit in a case where the head-mounted display is in the ultrasound image non-display mode.

20. A method of controlling an ultrasound system in which a mobile information terminal is connected to an ultrasound probe and a head-mounted display having a head-mounted display-side display unit, the method comprising:
generating a sound ray signal by directing a transducer array of the ultrasound probe to transmit and receive an ultrasonic wave based on an input operation through an input unit that includes a touch sensor disposed to be superimposed on a mobile information terminal-side display unit and is used by a user to perform the input operation;
generating image information data based on the generated sound ray signal;
transmitting the generated image information data from the ultrasound probe to the mobile information terminal in a wireless manner by using a first wireless communication system;
generating an operation image that is used by a user to perform the input operation;
displaying the operation image on the mobile information terminal-side display unit;
generating head-mounted display data having a display format for the head-mounted display-side display unit based on the image information data transmitted from the ultrasound probe in the wireless manner;
transmitting the generated head-mounted display data from the mobile information terminal to the head-mounted display in the wireless manner by using a second wireless communication system which is different from the first wireless communication system; and
displaying the head-mounted display ultrasound image on the head-mounted display-side display unit based on the head-mounted display data.

\* \* \* \* \*